US011565093B2

(12) United States Patent
Kirt et al.

(10) Patent No.: US 11,565,093 B2
(45) Date of Patent: Jan. 31, 2023

(54) INTRODUCER WITH EXPANDABLE CAPABILITIES

(71) Applicant: BOSTON SCIENTIFIC SCIMED, INC., Maple Grove, MN (US)

(72) Inventors: David Cory Kirt, Minnetonka, MN (US); Gregory Dyer, Maple Grove, MN (US); Adam David Grovender, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 375 days.

(21) Appl. No.: 16/565,714

(22) Filed: Sep. 10, 2019

(65) Prior Publication Data

US 2020/0078571 A1 Mar. 12, 2020

Related U.S. Application Data

(60) Provisional application No. 62/731,779, filed on Sep. 14, 2018, provisional application No. 62/729,238, filed on Sep. 10, 2018.

(51) Int. Cl.
*A61M 29/00* (2006.01)
*A61M 25/00* (2006.01)
(Continued)

(52) U.S. Cl.
CPC .......... *A61M 29/00* (2013.01); *A61B 17/3423* (2013.01); *A61M 25/001* (2013.01);
(Continued)

(58) Field of Classification Search
CPC ................ A61M 29/00; A61M 29/001; A61M 29/0045; A61M 29/007;
(Continued)

(56) References Cited

U.S. PATENT DOCUMENTS 4,531,943 A  7/1985  Van Tassel et al.
4,710,181 A  12/1987  Fuqua
(Continued)

FOREIGN PATENT DOCUMENTS

EP  2101661 B1  9/2009
EP  2995268 A1  3/2016
(Continued)

OTHER PUBLICATIONS

International Search Report and Written Opinion dated Apr. 21, 2016 for International Application No. PCT/US2016/016608.
(Continued)

*Primary Examiner* — Tan-Uyen T Ho
*Assistant Examiner* — Bridget E. Rabaglia
(74) *Attorney, Agent, or Firm* — Seager, Tufte & Wickhem LLP

(57) ABSTRACT

An introducer may include a layered tubular member having an inner liner including at least one folded portion extending along a distal region of the inner liner in a delivery configuration; a reinforcing member disposed over at least a portion of the inner liner, the reinforcing member including a plurality of longitudinal spines defining a plurality of openings disposed between adjacent longitudinal spines, wherein each folded portion is circumferentially overlapped by one of the plurality of openings; and an outer sheath disposed over the reinforcing member, wherein the outer sheath includes at least one perforation circumferentially overlapping each folded portion; and a tip member fixedly attached to a tapered distal region of the layered tubular member. The inner liner may extend to a distal end of the layered tubular member. At least a portion of each folded portion may terminate proximal of the distal end of the layered tubular member.

14 Claims, 13 Drawing Sheets

(51) Int. Cl.
*A61M 25/06* (2006.01)
*A61B 17/34* (2006.01)

(52) U.S. Cl.
CPC ....... *A61M 25/007* (2013.01); *A61M 25/0045* (2013.01); *A61M 25/0074* (2013.01); *A61M 2025/0024* (2013.01); *A61M 2025/0059* (2013.01); *A61M 2025/0681* (2013.01)

(58) Field of Classification Search
CPC .. A61M 2025/0074; A61M 2025/0024; A61M 2025/0059; A61M 2025/0681; A61M 17/3423; A61B 17/3423
USPC .......................................................... 606/198
See application file for complete search history.

(56) References Cited

U.S. PATENT DOCUMENTS

| | | | |
|---|---|---|---|
| 4,738,666 A | 4/1988 | Fuqua | |
| 4,921,479 A | 5/1990 | Grayzel | |
| 5,104,388 A | 4/1992 | Quackenbush | |
| 5,256,150 A | 10/1993 | Quiachon et al. | |
| 5,320,611 A | 6/1994 | Bonutti et al. | |
| 5,380,304 A | 1/1995 | Parker | |
| 5,489,277 A | 2/1996 | Tolkoff et al. | |
| 5,702,373 A | 12/1997 | Samson | |
| 5,810,776 A | 9/1998 | Bacich et al. | |
| 5,863,284 A | 1/1999 | Klein | |
| 5,968,068 A | 10/1999 | Dehadashtian et al. | |
| 5,997,508 A | 12/1999 | Lunn et al. | |
| 6,080,141 A | 6/2000 | Castro et al. | |
| 6,090,072 A | 7/2000 | Kratoska et al. | |
| 6,187,000 B1 | 2/2001 | Davison et al. | |
| 6,187,100 B1 | 2/2001 | Miura et al. | |
| 6,197,016 B1 | 3/2001 | Fourkas et al. | |
| 6,277,108 B1 | 8/2001 | McBroom et al. | |
| 6,358,238 B1 | 3/2002 | Sherry | |
| 6,443,979 B1 | 9/2002 | Stalker et al. | |
| 6,494,869 B1 | 12/2002 | Hand et al. | |
| 6,652,492 B1 | 11/2003 | Bell et al. | |
| 6,939,327 B2 | 9/2005 | Hall et al. | |
| 7,144,386 B2 | 12/2006 | Korkor et al. | |
| 7,226,451 B2 | 6/2007 | Shluzas et al. | |
| 7,309,334 B2 | 12/2007 | von Hoffmann | |
| 7,329,268 B2 | 2/2008 | Van Nguyen et al. | |
| 7,670,354 B2 | 3/2010 | Davison et al. | |
| 7,713,193 B2 | 5/2010 | Nance et al. | |
| 7,762,995 B2 | 7/2010 | Eversull et al. | |
| 7,766,820 B2 | 8/2010 | Core | |
| 7,780,692 B2 | 8/2010 | Nance et al. | |
| 7,837,692 B2 | 11/2010 | Mulholland et al. | |
| 7,837,769 B2 | 11/2010 | Lahr | |
| 7,879,024 B2 | 2/2011 | Thorstenson et al. | |
| 7,892,203 B2 | 2/2011 | Lenker et al. | |
| 7,963,952 B2 | 6/2011 | Wright, Jr. et al. | |
| 3,090,936 A1 | 1/2012 | Fallon et al. | |
| 8,092,481 B2 | 1/2012 | Nance et al. | |
| 3,252,015 A1 | 8/2012 | Leeflang et al. | |
| 3,317,817 A1 | 11/2012 | Davison et al. | |
| 3,337,518 A1 | 12/2012 | Nance et al. | |
| 8,449,527 B2 | 5/2013 | Thorstenson et al. | |
| 8,668,668 B2 | 3/2014 | Bishop et al. | |
| 8,690,936 B2 | 4/2014 | Nguyen et al. | |
| 8,725,088 B2 | 5/2014 | Ginsburg et al. | |
| 8,744,572 B1 | 6/2014 | Greenhut et al. | |
| 8,764,704 B2 | 7/2014 | Lenker et al. | |
| 8,790,387 B2 | 7/2014 | Nguyen et al. | |
| 8,894,615 B2 | 11/2014 | Voss | |
| 9,044,577 B2 | 6/2015 | Bishop et al. | |
| 9,089,669 B2 | 7/2015 | Haslinger et al. | |
| 9,168,060 B2 | 10/2015 | Voss | |
| 9,241,735 B2 | 1/2016 | Kick et al. | |
| 9,301,840 B2 | 4/2016 | Nguyen et al. | |
| 9,301,841 B2 | 4/2016 | Nguyen et al. | |
| 9,320,508 B2 | 4/2016 | Carroux | |
| 9,415,186 B2 | 8/2016 | Chebator et al. | |
| 9,801,657 B2 | 10/2017 | Furnish et al. | |
| 9,956,376 B2 | 5/2018 | Anderson et al. | |
| 2004/0006344 A1 | 1/2004 | Nguyen et al. | |
| 2004/0087968 A1 | 5/2004 | Core | |
| 2005/0124937 A1 | 6/2005 | Kick et al. | |
| 2005/0125021 A1 | 6/2005 | Nance et al. | |
| 2005/0216047 A1 | 9/2005 | Kumoyama et al. | |
| 2006/0135981 A1 | 6/2006 | Lenker et al. | |
| 2007/0021768 A1 | 1/2007 | Nance et al. | |
| 2008/0004521 A1 | 1/2008 | Hundley et al. | |
| 2008/0004571 A1 | 1/2008 | Voss | |
| 2008/0200943 A1 | 8/2008 | Barker et al. | |
| 2009/0043285 A1 | 2/2009 | Stehr et al. | |
| 2010/0082000 A1 | 4/2010 | Honeck et al. | |
| 2010/0094392 A1 | 4/2010 | Nguyen et al. | |
| 2010/0198160 A1 | 8/2010 | Voss | |
| 2012/0083877 A1 | 4/2012 | Nguyen et al. | |
| 2012/0323180 A1 | 12/2012 | Chebator et al. | |
| 2013/0079861 A1 | 3/2013 | Reinert et al. | |
| 2014/0236122 A1 | 8/2014 | Anderson et al. | |
| 2015/0238178 A1 | 8/2015 | Carroux | |
| 2016/0074067 A1 | 3/2016 | Furnish et al. | |
| 2016/0213882 A1* | 7/2016 | Fitterer | A61B 17/320758 |
| 2016/0296332 A1 | 10/2016 | Zhou et al. | |
| 2017/0252062 A1* | 9/2017 | Fitterer | A61B 17/3423 |
| 2018/0161064 A1 | 6/2018 | Fitterer et al. | |
| 2018/0199960 A1 | 7/2018 | Anderson et al. | |
| 2018/0221149 A1 | 8/2018 | Reynolds et al. | |
| 2018/0325548 A1 | 11/2018 | Haverkost et al. | |
| 2018/0325549 A1 | 11/2018 | Thoreson et al. | |
| 2019/0029825 A1 | 1/2019 | Fitterer et al. | |
| 2019/0083083 A1 | 3/2019 | Tassoni, Jr. et al. | |

FOREIGN PATENT DOCUMENTS

| | | |
|---|---|---|
| JP | H09501594 A | 2/1997 |
| JP | 2007054646 A | 3/2007 |
| JP | 2010530792 A | 9/2010 |
| JP | 2012040145 A | 3/2012 |
| JP | 2013116220 A | 6/2013 |
| WO | 9505207 A2 | 2/1995 |
| WO | 2004037333 A1 | 5/2004 |
| WO | 2006069215 A2 | 6/2006 |
| WO | 2008157830 A1 | 12/2008 |
| WO | 2009035745 A1 | 3/2009 |
| WO | 2010017537 A2 | 2/2010 |
| WO | 2016164082 A1 | 10/2016 |

OTHER PUBLICATIONS

International Search Report and Written Opinion dated May 15, 2017 for International Application No. PCT/US2017/020010.
International Search Report and Written Opinion dated Jul. 12, 2016 for International Application No. PCT/US2016/014401.
Invitation to pay Additional Fees dated Jul. 2, 2018 for International Application No. PCT/US2018/014147.
International Search Report and Written Opinion dated Mar. 8, 2018 for International Application No. PCT/US2017/065534.
International Search Report and Written Opinion dated Jan. 9, 2020 for International Application No. PCT/US2019/050344.

\* cited by examiner

INTRODUCER WITH EXPANDABLE CAPABILITIES

CROSS-REFERENCE TO RELATED APPLICATIONS

This application claims the benefit of priority under 35 U.S.C. § 119 to U.S. Provisional Application Ser. No. 62/729,238, filed Sep. 10, 2018, and U.S. Provisional Application Ser. No. 62/731,779, filed Sep. 14, 2018, the entirety of which is incorporated herein by reference.

TECHNICAL FIELD

The disclosure relates generally to medical devices and more particularly to medical devices that are adapted for use in percutaneous medical procedures.

BACKGROUND

In some instances, performing percutaneous medical procedures may require the insertion and/or maneuvering of relatively large medical devices through a patient's vasculature. However, inserting the medical device into the vasculature may result in undesirable forces being applied to the vessel walls. Therefore, it may be desirable to design an introducer having a reduced insertion profile, yet capable of expansion when necessary (e.g., during the passage of a medical device therethrough) to provide protection to the vessel wall. Of the known medical devices and methods, each has certain advantages and disadvantages. There is an ongoing need to provide alternative medical devices and introducers as well as alternative methods for manufacturing and using medical devices and introducers.

SUMMARY

In a first aspect, an introducer may comprise a layered tubular member, comprising: an inner liner including a lumen, a distal region, and at least one folded portion extending along the distal region of the inner liner in a delivery configuration; a reinforcing member disposed over at least a portion of the inner liner, the reinforcing member having a length and including a plurality of longitudinal spines defining a plurality of openings disposed between adjacent longitudinal spines, wherein each folded portion is circumferentially overlapped by one of the plurality of openings; and an outer sheath disposed over the reinforcing member, wherein the outer sheath includes at least one perforation circumferentially overlapping each folded portion; and a tip member fixedly attached to a tapered distal region of the layered tubular member. The inner liner may extend to a distal end of the layered tubular member. At least a portion of each folded portion may terminate proximal of the distal end of the layered tubular member.

In addition or alternatively, and in a second aspect, the inner liner is configured to radially expand from the delivery configuration to an expanded configuration.

In addition or alternatively, and in a third aspect, the lumen has a first diameter in the delivery configuration and a second diameter in the expanded configuration, the second diameter being greater than the first diameter.

In addition or alternatively, and in a fourth aspect, at least one of the at least one folded portion at least partially unfolds when the inner liner radially expands from the delivery configuration to the expanded configuration.

In addition or alternatively, and in a fifth aspect, wherein the layered tubular member includes a cut out radially aligned with each folded portion and extending proximally from the distal end of the layered tubular member within the tapered distal region.

In addition or alternatively, and in a sixth aspect, the tapered distal region of the layered tubular member tapers in a distal direction from a first outer diameter to a second outer diameter less than the first outer diameter.

In addition or alternatively, and in a seventh aspect, the inner liner is formed from an inelastic material.

In addition or alternatively, and in an eighth aspect, one or more of the plurality of longitudinal spines have a substantially constant width along the length of the reinforcing member.

In addition or alternatively, and in a ninth aspect, one or more of the plurality of longitudinal spines have a distally-reducing width along at least a portion of the length of the reinforcing member.

In addition or alternatively, and in a tenth aspect, a method of manufacturing an introducer may comprise: positioning a reinforcing member on a first mandrel, the reinforcing member having a length and including a plurality of longitudinal spines defining a plurality of openings disposed between adjacent longitudinal spines; disposing an outer sheath over the reinforcing member on the first mandrel, the outer sheath including at least one perforation circumferentially overlapping the plurality of openings; joining the outer sheath to the reinforcing member; wrapping an inner liner around a second mandrel to form a folded configuration having at least one folded portion extending along a distal region of the inner liner; disposing the outer sheath and the reinforcing member over at least a portion of the inner liner on the second mandrel to form a layered tubular member, wherein the at least one perforation circumferentially overlaps each folded portion; removing material about a circumference of the layered tubular member adjacent a distal end of the layered tubular member to form a tapered distal region of the layered tubular member; removing each folded portion from the inner liner within the tapered distal region; and fixedly attaching a tip member to the tapered distal region.

In addition or alternatively, and in an eleventh aspect, joining the outer sheath to the reinforcing member includes heating the reinforcing member and the outer sheath to induce reflow between the reinforcing member and the outer sheath.

In addition or alternatively, and in a twelfth aspect, the method may further comprise: prior to removing material about the circumference of the layered tubular member, heating the outer sheath, the reinforcing member, and the inner liner to induce reflow of the outer sheath and the reinforcing member about the inner liner, thereby joining the outer sheath and the reinforcing member to the inner liner to form the layered tubular member.

In addition or alternatively, and in a thirteenth aspect, removing each folded portion from the inner liner within the tapered distal region includes removing portions of the outer sheath that overlap each folded portion within the tapered distal region of the layered tubular member.

In addition or alternatively, and in a fourteenth aspect, the tip member is formed from a lower durometer material than the outer sheath, the reinforcing member, or the inner liner.

In addition or alternatively, and in a fifteenth aspect, the at least one perforation forms a preferred tear line along the outer sheath configured to split apart in response to expansion of the inner liner from the folded configuration toward an expanded configuration.

In addition or alternatively, and in a sixteenth aspect, an introducer may comprise a layered tubular member, comprising: an inner liner including a lumen, a distal region, and at least one folded portion extending along the distal region of the inner liner in a delivery configuration; a reinforcing member disposed over at least a portion of the inner liner, the reinforcing member having a length and including a plurality of longitudinal spines defining a plurality of openings disposed between adjacent longitudinal spines, wherein each folded portion is circumferentially overlapped by one of the plurality of openings; and an outer sheath disposed over the reinforcing member, wherein the outer sheath has a length and includes a plurality of windows radially aligned with each folded portion; and a tip member fixedly attached to a tapered distal region of the layered tubular member. The inner liner may extend to a distal end of the layered tubular member. The tapered distal region may be devoid of each folded portion.

In addition or alternatively, and in a seventeenth aspect, the tip member is configured to split apart where the tapered distal region is devoid of each folded portion when the inner liner radially expands from the delivery configuration towards an expanded configuration.

In addition or alternatively, and in an eighteenth aspect, the plurality of windows decreases in size from a distal end of the layered tubular member toward a proximal end of the layered tubular member.

In addition or alternatively, and in a nineteenth aspect, each of the plurality of windows are longitudinally separated by a distance, and wherein the distance varies along the length of the outer sheath.

In addition or alternatively, and in a twentieth aspect, the inner liner has a thickness, and wherein the thickness of the inner liner is maintained along a distal edge of the inner liner between adjacent longitudinal spines.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
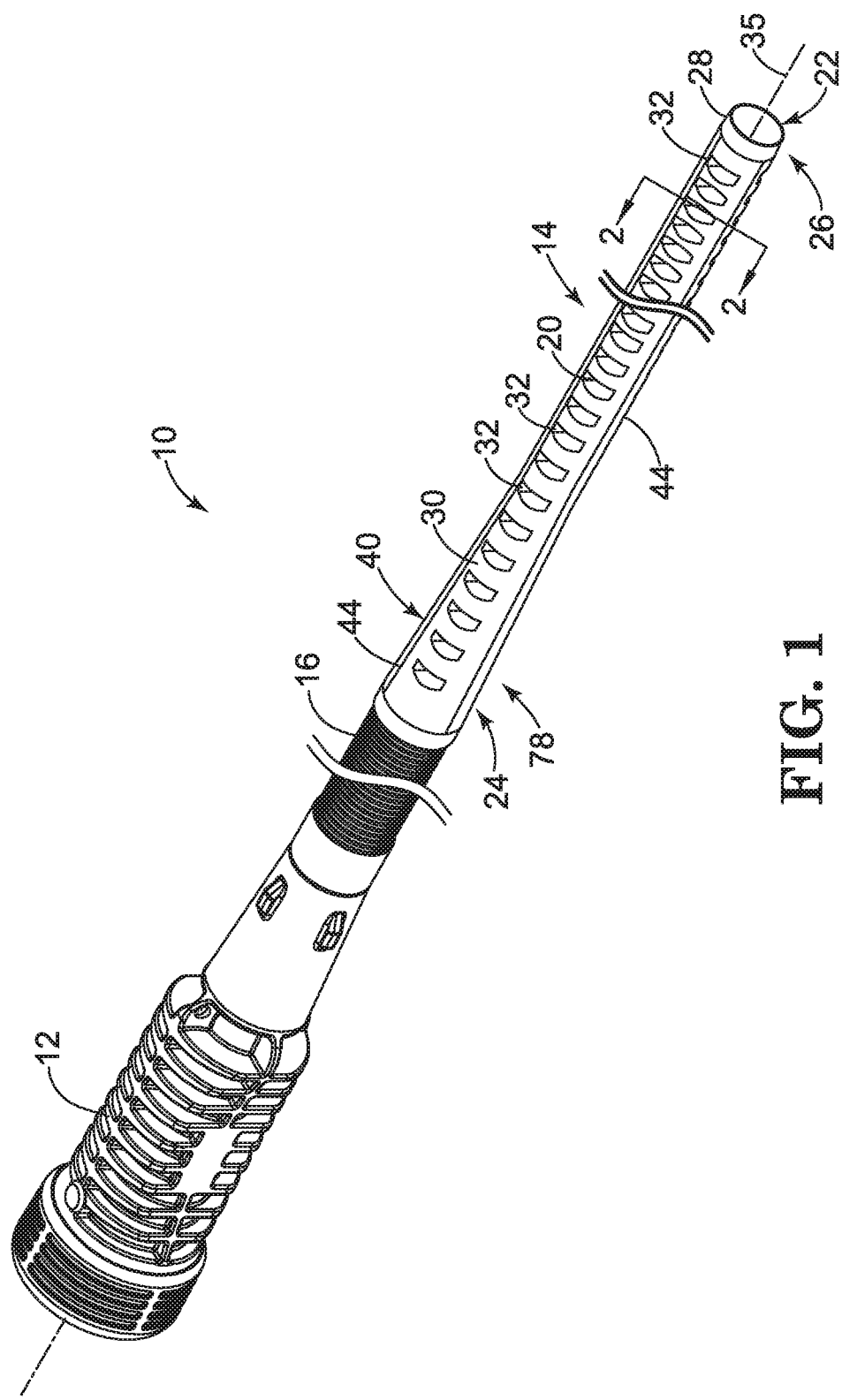
FIG. 1 illustrates aspects of an example introducer.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The figures illustrate selected components and/or arrangements of an introducer 10 (e.g., a delivery sheath, an access sheath, a tubular member, etc.), shown schematically in FIG. 1 for example. It should be noted that in any given figure, some features of the introducer 10 may not be shown, or may be shown schematically, for simplicity. Additional details regarding some of the components of the introducer 10 may be illustrated in other figures in greater detail. An introducer 10 may be used to facilitate delivery and/or deployment of a variety of medical implants (e.g., an occlusive medical implant, a replacement heart valve implant, etc.) to one or more locations within the anatomy, including but not limited to, in some embodiments, the heart. This, however, is not intended to be limiting as the introducer 10 may also be used for other interventions and/or percutaneous medical procedures within the vasculature of a patient. For example, devices and methods in accordance with the disclosure may be adapted for use in the digestive or gastrointestinal tract, such as in the mouth, throat, small and large intestine, colon, rectum, and the like. In another example, devices and methods in accordance with the disclosure may be adapted and configured for use within the respiratory tract, such as in the mouth, nose, throat, bronchial passages, nasal passages, lungs, and the like. Similarly, the devices and methods described herein with respect to percutaneous deployment may be used in other types of surgical procedures, as appropriate. For example, in some examples, the devices may be used in a non-percutaneous procedure. Devices and methods in accordance with the disclosure may also be adapted and configured for other uses within the anatomy.

In some embodiments, the introducer 10 may include a proximal hub 12 disposed proximate and/or at a proximal end of the introducer 10. In some embodiments, the introducer 10 may comprise a layered tubular member 14 extending distally from the proximal hub 12 toward and/or to a distal end of the introducer 10. In some embodiments, the introducer 10 may include a spring member 16 at least partially disposed between the proximal hub 12 and the layered tubular member 14.

In some embodiments, the layered tubular member 14 may include an inner liner 20 including a lumen 22 extending from a proximal region 24 to a distal region 26. In some embodiments, the lumen 22 may extend at least partially through the proximal region 24 and/or the distal region 26. In some embodiments, the lumen 22 may extend completely through the inner liner 20. In some embodiments, the inner liner 20 may have a substantially annular shape. In some embodiments, the inner liner 20 may have a compliant, elongated tubular structure. In some embodiments, the layered tubular member 14 may include an outer sheath 30 and/or a reinforcing member 40. In some embodiments, the reinforcing member 40 may be disposed over, around, and/or about at least a portion of the inner liner 20. In some embodiments, the outer sheath 30 may be disposed over, around, and/or about the reinforcing member 40 and/or the inner liner 20. Additional details regarding the inner liner 20, the outer sheath 30, and the reinforcing member 40 will be discussed herein. In some embodiments, the introducer 10 may include a tip member 28 fixedly attached at a distal end of the layered tubular member 14.

In some embodiments, the introducer 10 and/or the layered tubular member 14 has an outer diameter and may include a tapered region 78. In some embodiments, the tapered region 78 may be positioned proximal to the distal region 26 of inner liner 20. In some embodiments, at least a portion of the introducer 10 and/or the layered tubular member 14 may have a substantially constant outer diameter which transitions into the tapered region 78. In some embodiments, the substantially constant outer diameter may be disposed distal of the tapered region 78. At least a portion of the tapered region 78 may have an outer diameter which is greater than the substantially constant outer diameter of the introducer 10 and/or the layered tubular member 14 distal of the tapered region 78. However, this is not intended to be limiting. It is contemplated that any portion of the introducer 10 and/or the layered tubular member 14 may include any number of tapers, constant diameter regions, or combinations thereof.

In some embodiments, the proximal region 24 of the inner liner 20 and/or the outer sheath 30 may be attached to the spring member 16. In some embodiments, the inner liner 20 and/or the outer sheath 30 may cover an inner surface of the spring member 16, an outer surface of the spring member 16, or both the inner surface and the outer surface of the spring member 16. For example, in some embodiments, the spring member 16 may be positioned between the inner liner 20 and the outer sheath 30. Other configurations and/or arrangements are also contemplated.

In some embodiments, the spring member 16, the inner liner 20, and/or the outer sheath 30 may be fixedly attached to the proximal hub 12. The proximal hub 12 may include a hemostatic valve or seal disposed therein. The hemostatic valve or seal may prevent blood, other bodily fluid(s), and/or other fluid(s) (e.g., irrigation fluid, etc.) from flowing proximally through the lumen 22 of the inner liner 20. In some embodiments, the proximal hub 12 may include at least one port in fluid communication with the lumen 22 of the inner liner 20.

FIG. 1 illustrates the outer sheath 30 and the reinforcing member 40 fixedly attached to the inner liner 20. As will be evident from the discussion herein, both the outer sheath 30 and the reinforcing member 40 may be disposed, attached, and/or fixedly attached, etc. along the inner liner 20 from the distal region 26 to the proximal region 24. The outer sheath 30 may include at least one perforation 32 (e.g., at least one aperture, at least one window, at least one opening, etc.) extending along at least a portion of a wall of the outer sheath 30 and/or extending along at least a portion of a length of the outer sheath 30. Additional details regarding the at least one perforation 32 are described herein. In at least some embodiments, the at least one perforation 32 may be aligned with a central longitudinal axis 35 of the introducer 10, the layered tubular member 14, the lumen 22 of the inner liner 20, and/or the outer sheath 30. The layered tubular member 14, the inner liner 20, the outer sheath 30, and/or the reinforcing member 40 may be arranged and/or positioned coaxially with the central longitudinal axis 35. The reinforcing member 40 may include a plurality of longitudinal spines 44. Each of the at least one perforation 32 may be circumferentially disposed and/or positioned between adjacent longitudinal spines 44 of the plurality of longitudinal spines 44 of the reinforcing member 40.

Figure 2:
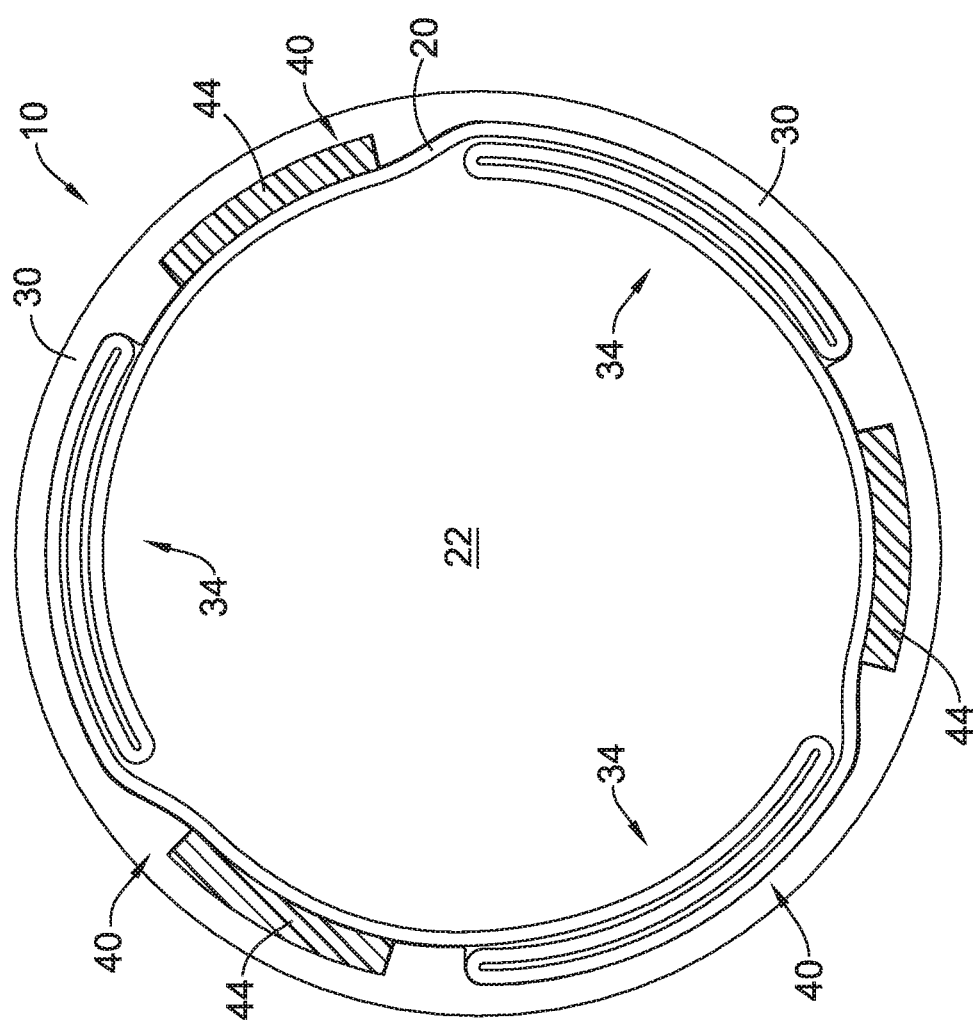
FIG. 2 is a cross-sectional view taken through the line 2-2 of FIG. 1.

As shown in FIG. 2 for example, the inner liner 20 may include a wall having an outer surface and an inner surface defining the lumen 22. A thickness of the wall of the inner liner 20 may be defined by the inner surface and the outer surface of the inner liner 20. The inner liner 20 may include at least one folded portion 34 extending along the distal region 26 of the inner liner 20 in a delivery configuration and/or a folded configuration. In some embodiments, the at least one folded portion 34 may extend along the proximal region 24 and the distal region 26 of the inner liner 20 in the delivery configuration and/or the folded configuration. In some embodiments, the at least one folded portion 34 may extend along an entire length of the inner liner 20 in the delivery configuration and/or the folded configuration. In one example shown in FIG. 2, the at least one folded portion 34 includes three folded portions 34, but it is contemplated that the inner liner 20 may include greater or less than three folded portions 34. For example, the at least one folded portion 34 may include two folded portions 34, three folded portions 34, four folded portions 34, five folded portions 34, or more folded portions 34, as desired in a particular configuration. The inner liner 20 may be disposed radially inward of the outer sheath 30. In some embodiments, each of and/or some of the at least one folded portion 34 may fold back on itself to form, for example, a wave shape, an S-shape, a T-shape, a Z-shape, and/or combinations of these when viewed in cross-section in the delivery configuration and/or the folded configuration. Other shapes and/or configurations are also contemplated.

In the delivery configuration, the inner liner 20 may have a generally annular shape. Other shapes and/or configurations are also contemplated. In the delivery configuration and/or the folded configuration, the lumen 22 of the inner liner 20 may have a first inner diameter and/or a first inner extent measured through and normal to the central longitudinal axis 35 defined by the inner surface of the inner liner 20. The inner liner 20 may be configured to radially expand from the delivery configuration and/or the folded configuration to an expanded configuration (e.g., FIG. 13) when subjected to a radially outward force from within the lumen 22 of the inner liner 20. In the expanded configuration, the lumen 22 of the inner liner 20 may have a second inner diameter greater than the first inner diameter and/or a second inner extent measured through and normal to the central longitudinal axis 35 that is greater than the first inner extent. At least one of the at least one folded portion 34 may at least partially unfold when the inner liner 20 radially expands from the delivery configuration and/or the folded configuration to the expanded configuration. Similarly, in the delivery configuration and/or the folded configuration, the inner liner 20 may have a first outer diameter and/or a first outer extent measured through and normal to the central longitudinal axis 35 defined by the outer surface of the inner liner 20. In the expanded configuration, the inner liner 20 may have a second outer diameter greater than the first outer diameter and/or a second outer extent measured through and normal to the central longitudinal axis 35 that is greater than the first outer extent. In some embodiments, the inner liner 20 may be configured to permit the lumen 22 to radially expand from the first inner diameter and/or the first inner extent to the second inner diameter and/or the second inner extent when subjected to the radially outward force from within the lumen 22 of the inner liner 20. In some embodiments, the inner liner 20 may be configured to expand radially outward from the first inner diameter and/or the first inner extent to a predetermined second inner diameter and/or a predetermined second inner extent. For example, the second inner diameter and/or the second inner extent may have a predetermined value, and the inner liner 20 may be configured to prevent stretching or expanding radially outward beyond the predetermined value.

In at least some embodiments, the inner liner 20 may be substantially and/or completely compliant, and/or the inner liner 20 may have no radial self-bias. For example, the inner liner 20 may have no radially inward self-bias and/or no radially outward self-bias. In at least some embodiments, the inner liner 20 may be non-self-supporting and may not include a mechanism to radially expand and/or open on its own (e.g., absent a radially outward force exerted upon the inner liner 20 from inside the lumen 22). For example, the inner liner 20 may require a device or object (e.g., a dilator, a medical device or sheath, etc.) that has a greater outer diameter than the first inner diameter and/or the first inner extent of the lumen 22 of the inner liner 20 to push and/or urge the inner liner 20 radially outward from the delivery configuration and/or the folded configuration toward the expanded configuration. Additionally, in some embodiments, the inner liner 20 may not require a radially inward force to be applied to the outer surface of the inner liner 20 to collapse radially inward when there is no device, object, etc. disposed within the lumen 22 of the inner liner 20. For example, the inner liner 20 may not be held open or maintain a particular expanded size on its own, or the inner liner 20 may be non-self-supporting. Similarly, the inner liner 20 may not be biased to collapse radially inwardly on its own. For example, the inner liner 20 may take the shape and/or form of, and/or the outer surface of the inner liner 20 may align with and/or be in contact with, surrounding tissue(s) after being expanded from the delivery configuration and/or the folded configuration toward and/or into the expanded configuration. In one example, a constriction in or of a vessel or body lumen in which the inner liner 20 is disposed may urge the inner liner 20 radially inward in the absence of the force, object, device, etc. that expanded the inner liner 20, but the inner liner 20 is not self-biased radially inwardly on its own (e.g., the inner liner 20 may have zero return force after expanding/opening).

In some embodiments, the inner liner 20 may be formed from a compliant material. In some embodiments, the inner liner 20 may be formed from an inelastic material. In another embodiment, the inner liner 20 may be formed from an elastic material or a combination of inelastic and elastic materials. In some embodiments, the inner liner 20 may be configured to prevent axial stretching of the inner liner 20 along the lumen 22. For example, the inner liner 20 may be configured to expand radially outward from the central longitudinal axis 35 without stretching or expanding in an axial or longitudinal direction along the central longitudinal axis 35. In some embodiments, the inner liner 20 may be formed from a polymeric and/or plastic material. In some embodiments, the inner liner 20 may be formed from a non-thermoplastic material designed to resist melting while heat is applied to reflow other and/or adjacent components as discussed herein. For example, in at least some embodiments, the inner liner 20 may be formed from a material that has a higher melting point than the reinforcing member 40 and/or the outer sheath 30. Some suitable, but non-limiting, examples of materials for the inner liner 20 are discussed below. In some embodiments, the inner surface of the wall of the inner liner 20 may include one or more layers or coatings, such as but not limited to, a lubricious coating, a hydrophilic coating, a hydrophobic coating, and/or other suitable coatings and the like. In some embodiments, the inner liner 20 may include a lubricant disposed on the inner surface of the wall of the inner liner 20 and/or within the lumen 22 of the inner liner 20. In some embodiments, an outer surface of the introducer 10 and/or the outer sheath 30 may include one or more layers or coatings, such as but not limited to, a lubricious coating, a hydrophilic coating, a hydrophobic coating, and/or other suitable coatings and the like. In some embodiments, the introducer 10 and/or the outer sheath 30 may include a lubricant disposed on the outer surface of the introducer 10 and/or the outer sheath 30.

Figure 3:
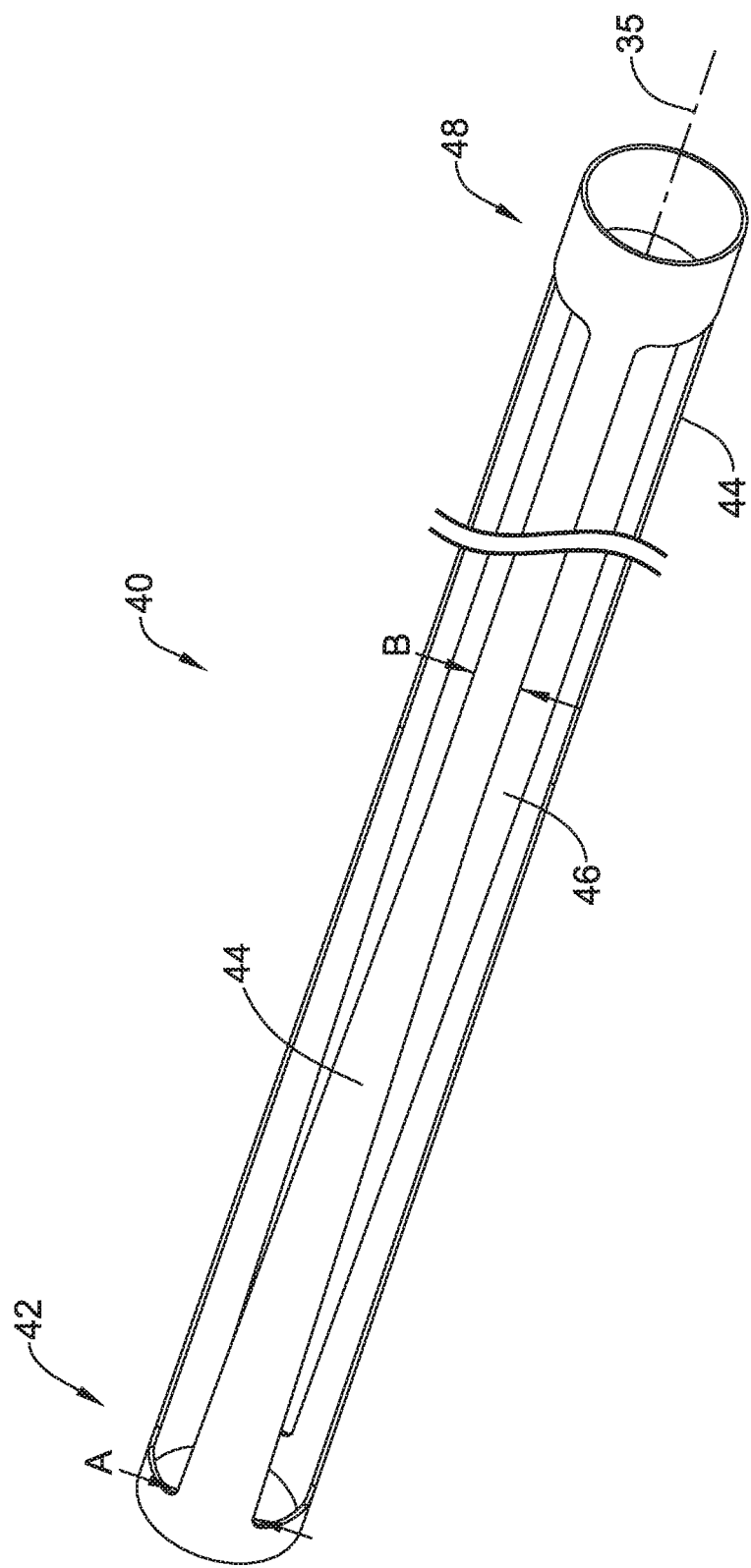
FIG. 3 illustrates aspects of an example reinforcing member associated with the introducer of FIG. 1.

The reinforcing member 40 may include a plurality of longitudinal spines 44 defining a plurality of openings 46 disposed between adjacent longitudinal spines 44, as seen in FIG. 3 for example. The plurality of longitudinal spines 44 may extend from a proximal end 42 of the reinforcing member 40 to a distal end 48 of the reinforcing member 40. In at least some embodiments, during initial manufacture and/or forming of the reinforcing member 40, the plurality of longitudinal spines 44 may be integrally connected to each other at the proximal end 42 by a proximal circumferential ring and the distal end 48 by a distal circumferential ring. In some embodiments, during manufacturing and/or assembly of the layered tubular member 14, the proximal circumferential ring and/or the distal circumferential ring may be removed from the reinforcing member 40. In one example shown in FIG. 3, the reinforcing member 40 and/or the plurality of longitudinal spines 44 includes three longitudinal spines 44, but it is contemplated that the reinforcing member 40 and/or the plurality of longitudinal spines 44 may include greater or less than three longitudinal spines 44. For example, the reinforcing member 40 and/or the plurality of longitudinal spines 44 may include two longitudinal spines 44, three longitudinal spines 44, four longitudinal spines 44, five longitudinal spines 44, or more longitudinal spines 44, as desired in a particular configuration. In some embodiments, each of the plurality of longitudinal spines 44 may include a given wall thickness at various locations along its length. In some embodiments, the wall thickness of any of the plurality of longitudinal spines 44 described herein may vary along its length.

In some embodiments, one or more of the plurality of longitudinal spines 44 may include a variable width along the axial length of the reinforcing member 40 and/or the plurality of longitudinal spines 44. For example, FIG. 3 shows one or more of the plurality of longitudinal spines 44 having a first width A at a first axial location and a second width B at a second axial location, wherein the first axial location is proximal of the second axial location. In some embodiments, the first axial location may be proximate the proximal end 42 of the reinforcing member 40 and the second axial location may be proximate the distal end 48 of the reinforcing member 40. Other configurations are also contemplated. In some embodiments, the first width A may be greater than the second width B. Alternatively, the first width A may be less than the second width B. In some embodiments, one or more of the plurality of longitudinal spines 44 may taper along the axial length of the reinforcing member 40 and/or the plurality of longitudinal spines 44. For example, one or more of the plurality of longitudinal spines 44 may taper proximally, distally, and/or a combination thereof. In some embodiments, one or more of the plurality of longitudinal spines 44 may have a distally-reducing width (e.g., from the first width A to the second width B) along at least a portion of the axial length of the reinforcing member 40 and/or the plurality of longitudinal spines 44. In some embodiments, one or more of the plurality of longitudinal spines 44 may each have a distally-reducing width (e.g., from the first width A to the second width B) along at least a portion of the axial length of the reinforcing member 40 and/or the plurality of longitudinal spines 44. In some embodiments, the second width B may remain substantially constant along at least a portion of the axial length of the reinforcing member 40 and/or the plurality of longitudinal spines 44. In one example, one or more of the plurality of longitudinal spines 44 may be circumferentially spaced equally and/or equidistant around the central longitudinal axis 35 and/or the reinforcing member 40. In some examples, one or more of the plurality of longitudinal spines 44 may be irregularly and/or progressively spaced around the central longitudinal axis 35. Some suitable, but non-limiting, examples of materials for the reinforcing member 40 are discussed below.

Figure 4:
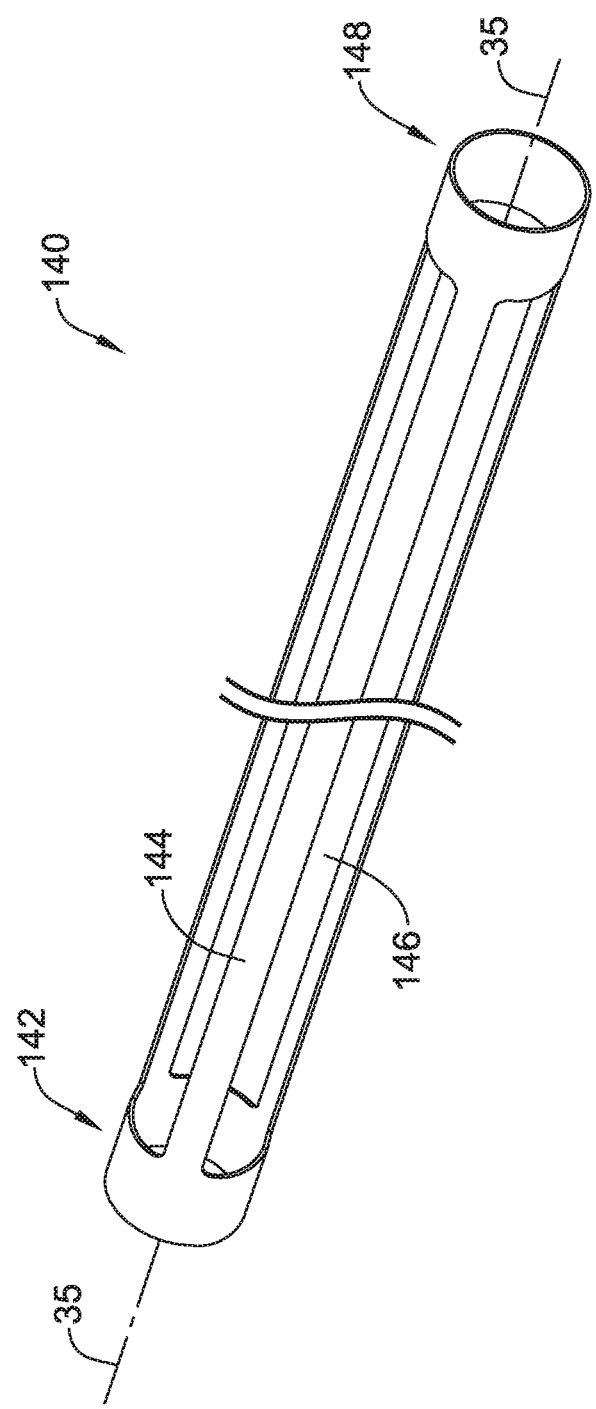
FIG. 4 illustrates aspects of an alternative reinforcing member associated with the introducer of FIG. 1.

FIG. 4 illustrates an alternative reinforcing member 140 including a plurality of longitudinal spines 144 defining a plurality of openings 146 disposed between adjacent longitudinal spines 144. The plurality of longitudinal spines 144 may extend from a proximal end 142 of the reinforcing member 140 to a distal end 148 of the reinforcing member 140. In at least some embodiments, during initial manufacture and/or forming of the reinforcing member 140, the plurality of longitudinal spines 144 may be integrally connected to each other at the proximal end 142 by a proximal circumferential ring and the distal end 148 by a distal circumferential ring. In some embodiments, during manufacturing and/or assembly of the layered tubular member 14, the proximal circumferential ring and/or the distal circumferential ring may be removed from the reinforcing member 140. In one example shown in FIG. 4, the reinforcing member 140 and/or the plurality of longitudinal spines 144 includes three longitudinal spines 144, but it is contemplated that the reinforcing member 140 and/or the plurality of longitudinal spines 144 may include greater or less than three longitudinal spines 144. For example, the reinforcing member 140 and/or the plurality of longitudinal spines 144 may include two longitudinal spines 144, three longitudinal spines 144, four longitudinal spines 144, five longitudinal spines 144, one or more longitudinal spines 144, as desired in a particular configuration. In some embodiments, each of the plurality of longitudinal spines 144 may include a given wall thickness at various locations along its length. In some embodiments, the wall thickness of any of the plurality of longitudinal spines 44 described herein may vary along its length. In the example of FIG. 4, one or more of the plurality of longitudinal spines 144 may include a substantially constant width along the axial length of the reinforcing member 140 and/or the plurality of longitudinal spines 144. In one example, the plurality of longitudinal spines 144 may be circumferentially spaced equally and/or equidistant around the central longitudinal axis 35 and/or the reinforcing member 140. In some examples, the plurality of longitudinal spines 144 may be irregularly and/or progressively spaced around the central longitudinal axis 35. It will be appreciated and understood that the reinforcing member 140 may be used in place of and/or interchangeably with the reinforcing member 40 throughout the disclosure. Some suitable, but non-limiting, examples of materials for the reinforcing member 140 are discussed below.

Figure 5:
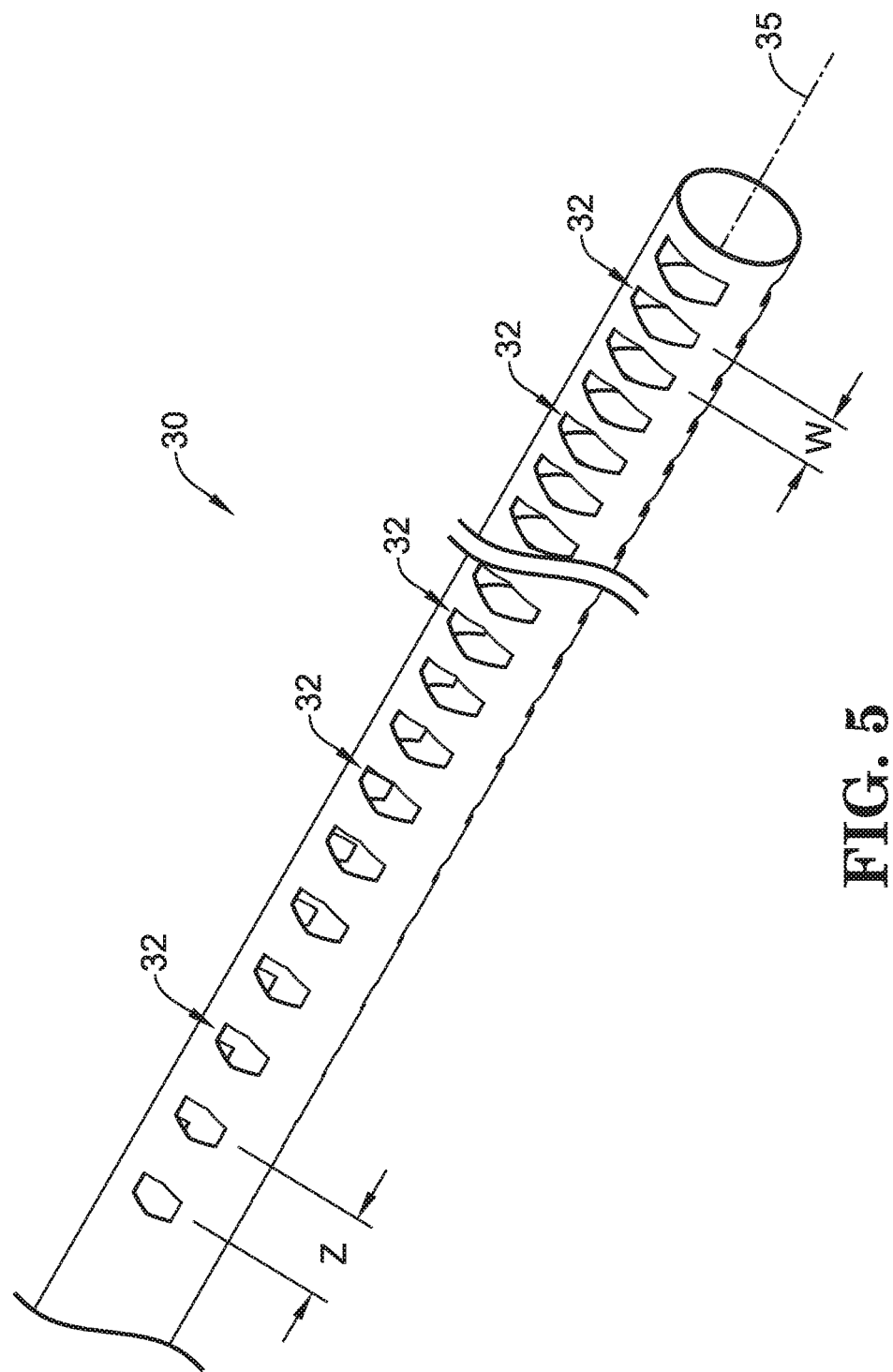
FIG. 5 illustrates aspects of an example outer sheath associated with the introducer of FIG. 1.

FIG. 5 illustrates one example of the outer sheath 30. In some embodiments, the outer sheath 30 may include at least one perforation 32 formed in and/or extending along at least a portion of the wall of the outer sheath 30 and/or extending along at least a portion of the length of the outer sheath 30. In some embodiments, the at least one perforation 32 may include and/or define a plurality of elements (e.g., a plurality of apertures, a plurality of windows, a plurality of openings, a plurality of notches, a plurality of holes, a plurality of weakening features, etc.) therein. In some embodiments, the at least one perforation may extend laterally and/or transversely through the wall of the outer sheath 30. For example, the at least one perforation 32 may effectively remove at least a portion of the wall of the outer sheath 30. In some embodiments, the at least one perforation 32 may only partially extend laterally and/or transversely through the wall of the outer sheath 30, so as to form an area of reduced wall thickness of the outer sheath 30. For example, in some embodiments, the at least one perforation 32 may extend through the wall of the outer sheath 30, while in other embodiments, the at least one perforation 32 may be formed as a substantially "thinner" section of the wall of the outer sheath 30. In some embodiments, the outer sheath 30 may extend continuously around the circumference of the inner liner 20 and/or the reinforcing member 40. In some embodiments, at least a portion of the outer sheath 30 may be discontinuous.

In some embodiments, the at least one perforation 32 forms a preferred and/or preferential tear line along the outer sheath 30 configured to split apart in response to expansion of the inner liner 20 from the delivery configuration and/or the folded configuration toward the expanded configuration. In some embodiments, the outer sheath 30 may be configured to separate, split, perforate, and/or tear as the inner liner 20 is expanded radially outward from the delivery configuration and/or the folded configuration toward the expanded configuration. In some embodiments, the outer sheath 30 may be configured to separate, split, perforate, and/or tear along and/or through the at least one perforation 32 formed in the wall of the outer sheath 30. In some embodiments, the outer sheath 30 may be configured to separate, split, perforate, and/or tear where the outer sheath 30 is discontinuous and/or constructed of and/or formed from a thinner material.

In at least some embodiments, the at least one perforation 32 may be axially aligned with the central longitudinal axis 35 of the introducer 10, the layered tubular member 14, the lumen 22 of the inner liner 20, and/or the outer sheath 30. In some embodiments, the outer sheath 30 includes at least one perforation 32 disposed over, radially aligned with, and/or circumferentially overlapping each folded portion 34 of the inner liner 20. In some embodiments, the at least one perforation 32 may be arranged in one or more longitudinal and/or axial lines along the length of the outer sheath 30, the layered tubular member 14, and/or the introducer 10. In some embodiments, the one or more longitudinal and/or axial lines may directly correspond to the at least one folded portion 34.

The outer sheath 30 may include a given wall thickness at various locations along its length. In some embodiments, the wall thickness of the outer sheath 30 may vary along its length. In some embodiments, the wall thickness of the outer sheath 30 may be tapered about the circumference of the inner liner 20 such that a reduced thickness region of the outer sheath 30 is disposed adjacent to, radially outward of, circumferentially aligned with, in communication with, and/or directly over the at least one folded portion 34. In some embodiments, the reduced thickness region is the at least one perforation 32.

In some embodiments, the at least one perforation 32 may have a polygonal shape, a regular shape, an irregular shape, a round shape, a triangular shape, a square or rectangular shape, a hexagonal shape, an octagonal shape, a trapezoidal shape, a diamond shape, or any other suitable shape. In some embodiments, the at least one perforation may be spaced apart from each other axially, longitudinally, and/or circumferentially, etc. In the example shown in FIG. 5, the at least one perforation 32 proximate a distal end of the outer sheath 30 may have elements thereof spaced apart from each other by a first distance W. In some embodiments, the at least one perforation 32 proximate a proximal end of the outer sheath 30 may have elements thereof spaced apart from each other by a second distance Z, wherein the second distance Z is greater than the first distance W. In some embodiments, the first distance W may be greater than the second distance Z. In some embodiments, the first distance W and the second distance Z may be substantially equal. In some embodiments, spacing between adjacent element of the at least one perforation may vary along the axial length of the outer sheath 30. For example, in some embodiments, spacing between adjacent elements may gradually increase, gradually decrease, and/or combinations thereof along the axial length of the outer sheath 30. In one example, the at least one perforation 32 may include a plurality of windows, wherein each of the plurality of windows are longitudinally separated by a distance, and wherein the distance varies along the length of the outer sheath 30.

In some embodiments, the at least one perforation may have and/or define a surface area. As used herein, the term "surface area", with respect to the at least one perforation, may be defined as the "area" bounded by the shape, outline, and/or perimeter of one of the at least one perforation 32. For example, in an embodiment where the at least one perforation 32 each has a polygonal shape, the "surface area" of a given element may be defined as the area bounded by an individual polygon. In some embodiments, the surface area of the at least one perforation 32 may be constant and/or equal along the length of the outer sheath 30. In some embodiments, the surface area of the at least one perforation 32 may vary along the length of the outer sheath 30. For example, with respect to the at least one perforation 32 illustrated in FIG. 5, the surface area proximate the distal end of the outer sheath 30, the layered tubular member 14, and/or the introducer 10 is greater than the surface area of the at least one perforation 32 proximal the proximal end of the outer sheath 30, the layered tubular member 14, and/or the introducer 10. In some embodiments, the surface area of the at least one perforation 32 may decrease gradually from the distal end of the outer sheath 30, the layered tubular member 14, and/or the introducer 10 toward the proximal end of the outer sheath 30, the layered tubular member 14, and/or the introducer 10. In one example, the at least one perforation 32 may include a plurality of windows, and the plurality of windows may decrease in size from the distal end of the outer sheath 30, the layered tubular member 14, and/or the introducer 10 toward the proximal end of the outer sheath 30, the layered tubular member 14, and/or the introducer 10. Other configurations, including but not limited to combinations of the features described herein, are also contemplated.

In some embodiments the outer sheath 30 may be formed from a polymeric material. In some examples, the outer sheath 30 may be formed from the same polymeric material as the inner liner 20. In some examples, the outer sheath 30 may be formed from a different polymeric material than the inner liner 20. In some embodiments, at least some of the outer sheath 30 may be fixedly attached to the outer surface of the wall of the inner liner 20, the reinforcing member 40, and/or the plurality of longitudinal spines 44. In some embodiments, the entire outer sheath 30 may be fixedly attached to the outer surface of the wall of the inner liner 20, the reinforcing member 40, and/or the plurality of longitudinal spines 44. Some suitable, but non-limiting, examples of materials for the outer sheath 30 are discussed below.

Figure 6:
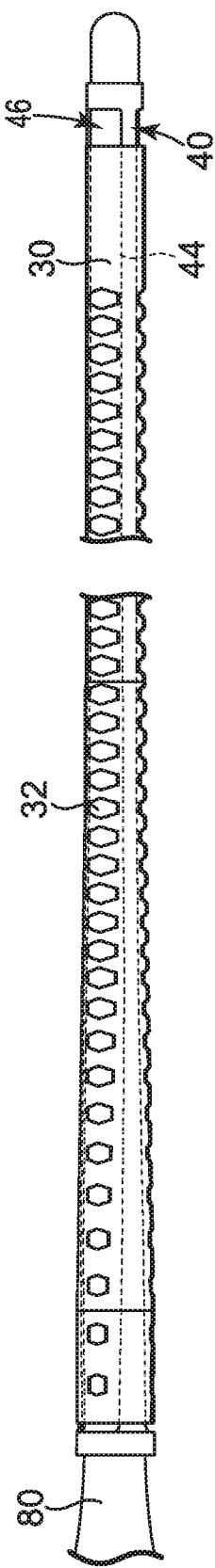
FIGS. 6-11 illustrate aspects of the construction of and a method of manufacturing the introducer of FIG. 1.

A method of manufacturing an introducer having a proximal end and a distal end may include positioning the reinforcing member 40 on a first mandrel 80. The reinforcing member 40 may have a length and include the plurality of longitudinal spines 44 defining the plurality of openings 46 disposed between adjacent longitudinal spines 44. The method may include disposing the outer sheath 30 over the reinforcing member 40 on the first mandrel 80, the outer sheath 30 including the at least one perforation 32 circumferentially overlapping the plurality of openings 46, as shown in FIG. 6 for example. As may also be seen in FIG. 6, the at least one perforation 32 may be formed in one or more longitudinal lines, and the plurality of longitudinal spines 44 may be positioned between the one or more longitudinal lines of the at least one perforation 32 such that the plurality of longitudinal spines 44 do not overlap, impinge upon, and/or cover any portion of the at least one perforation 32. For example, the at least one perforation 32 may be completely free of interference with any portion of the reinforcing member 40 and/or the plurality of longitudinal spines 44. The proximal circumferential ring and the distal circumferential ring of the reinforcing member 40 may be disposed outside of the outer sheath 30. For example, the proximal circumferential ring of the reinforcing member 40 may be disposed proximal of the outer sheath 30 and the distal circumferential ring of the reinforcing member 40 may be disposed distal of the outer sheath 30. As such, the plurality of longitudinal spines 44 may extend axially and/or longitudinally completely through the outer sheath 30. In at least some embodiments, at least a portion of each of the plurality of openings 46 may extend beyond (e.g., proximally and/or distally) of the outer sheath 30.

In some embodiments, a shrink wrap may then be applied over the first mandrel 80 and the outer sheath 30 and the reinforcing member 40. The method may include joining the outer sheath 30 to the reinforcing member 40. In some embodiments, joining the outer sheath 30 to the reinforcing member 40 may include heating the outer sheath 30 and the reinforcing member 40 shrink-wrapped on the first mandrel 80 to induce reflow between the reinforcing member 40 and the outer sheath 30. In some embodiments, the outer sheath 30 and the reinforcing member 40 may be at least partially tacked, glued, bonded, welded, or otherwise fixedly attached to each other prior to shrink wrapping, heating, and/or inducing reflow therebetween. Heating and/or reflowing the outer sheath 30 and the reinforcing member 40 may permit the outer sheath 30 to at least partially melt around and/or bond with the reinforcing member 40, thereby forming a smooth, coincident inner surface, wherein an inner surface of the outer sheath 30 and an inner surface of the reinforcing member 40 are substantially radially aligned with each other along a common inner circumference. For example, at least a portion of the outer sheath 30 may be in contact with the first mandrel 80 around the reinforcing member 40 after heating and/or reflow. In some embodiments, heating and/or reflowing the outer sheath 30 and/or the reinforcing member 40 may permit the outer sheath 30 to melt and/or partially fill in the at least one perforation 32. For example, in some embodiments, the outer sheath 30 may have a reduced wall thickness at and/or within the at least one perforation 32. In at least some embodiments, the at least one perforation 32 may still lack a wall thickness within at least a portion of the at least one perforation 32 after the heating and/or reflowing operation. In some embodiments, the heating and/or reflowing operation may reduce the surface area of the at least one perforation 32 along the length of the outer sheath 30.

The outer sheath 30 and the reinforcing member 40 may then be removed from the first mandrel 80 as a joined and/or fixedly attached assembly. In some embodiments, the shrink wrap may be removed before removing the outer sheath 30 and the reinforcing member 40 from the first mandrel 80, and in other embodiments, the shrink wrap may be removed after removing the outer sheath 30 and the reinforcing member 40 from the first mandrel 80. After removing the shrink wrap, the distal circumferential ring of the reinforcing member 40 may be removed, as the plurality of longitudinal spines 44 is now fixed and/or held in place by the reflowed outer sheath 30.

Figure 7:
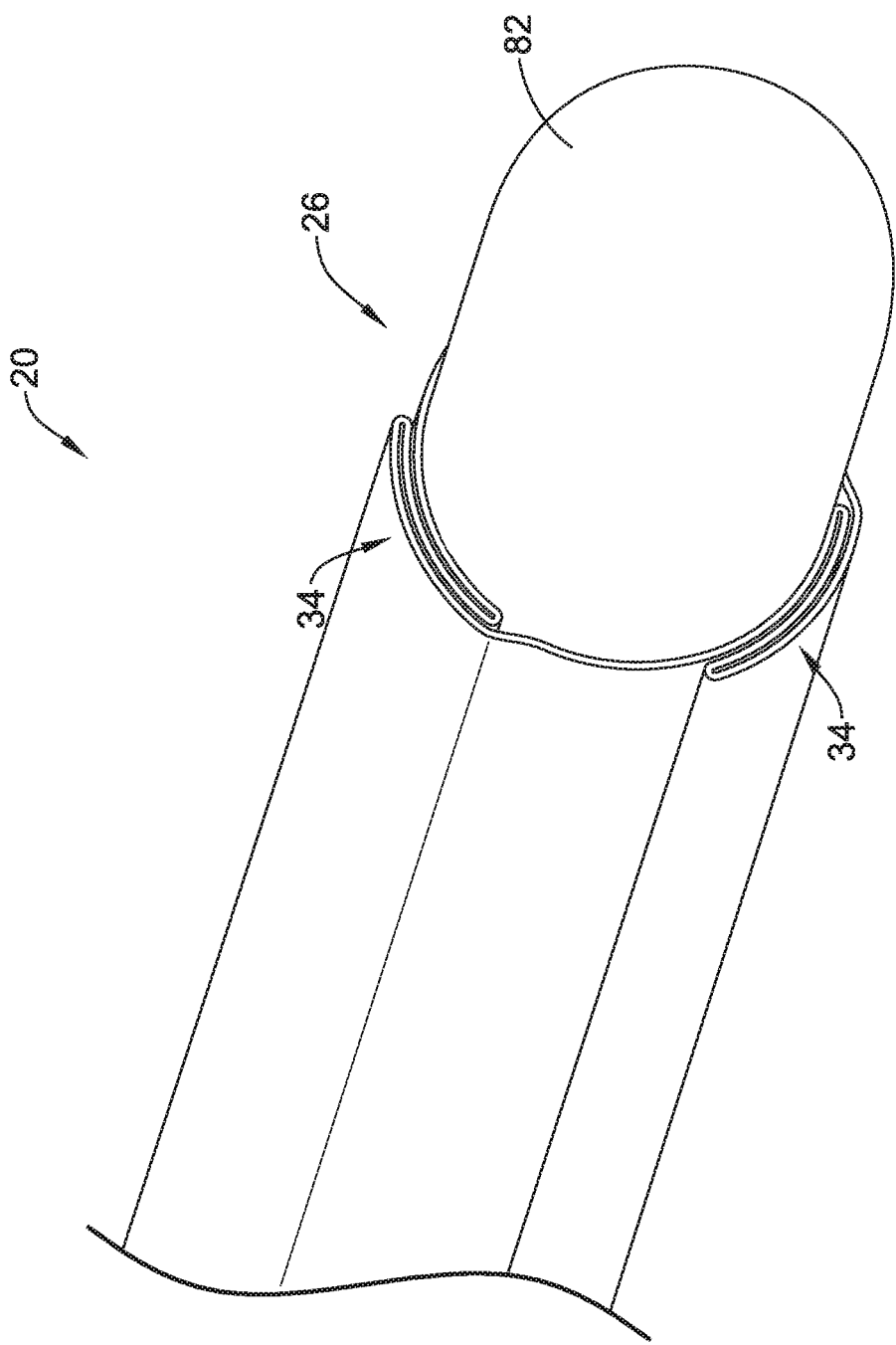

In some embodiments, the method of manufacturing the introducer 10 may include wrapping the inner liner 20 around a second mandrel 82 to form the delivery configuration and/or the folded configuration of the inner liner 20 having at least one folded portion 34 extending along the distal region 26 of the inner liner 20, as shown in FIG. 7 for example. In some embodiments, the at least one folded portion 34 may project radially outward slightly from the inner liner 20 and/or the second mandrel 82 immediately following wrapping the inner liner 20 around the second mandrel 82. In some embodiments, the outer surface of the wall of the inner liner 20 may be etched, chemically modified, mechanically modified, and/or otherwise processed to promote adhesion and/or bonding of the outer sheath 30 and/or the reinforcing member 40 to the inner liner 20. In some embodiments, the inner surface of the outer sheath 30 and/or the reinforcing member 40 may be etched, chemically modified, mechanically modified, and/or otherwise processed to promote adhesion and/or bonding of the outer sheath 30 and/or the reinforcing member 40 to the inner liner 20. In some embodiments, both the outer surface of the wall of the inner liner 20 and the inner surface of the outer sheath 30 and/or the reinforcing member 40 may be etched, chemically modified, mechanically modified, and/or otherwise processed to promote adhesion and/or bonding of the outer sheath 30 and/or the reinforcing member 40 to the inner liner 20.

Figure 8:
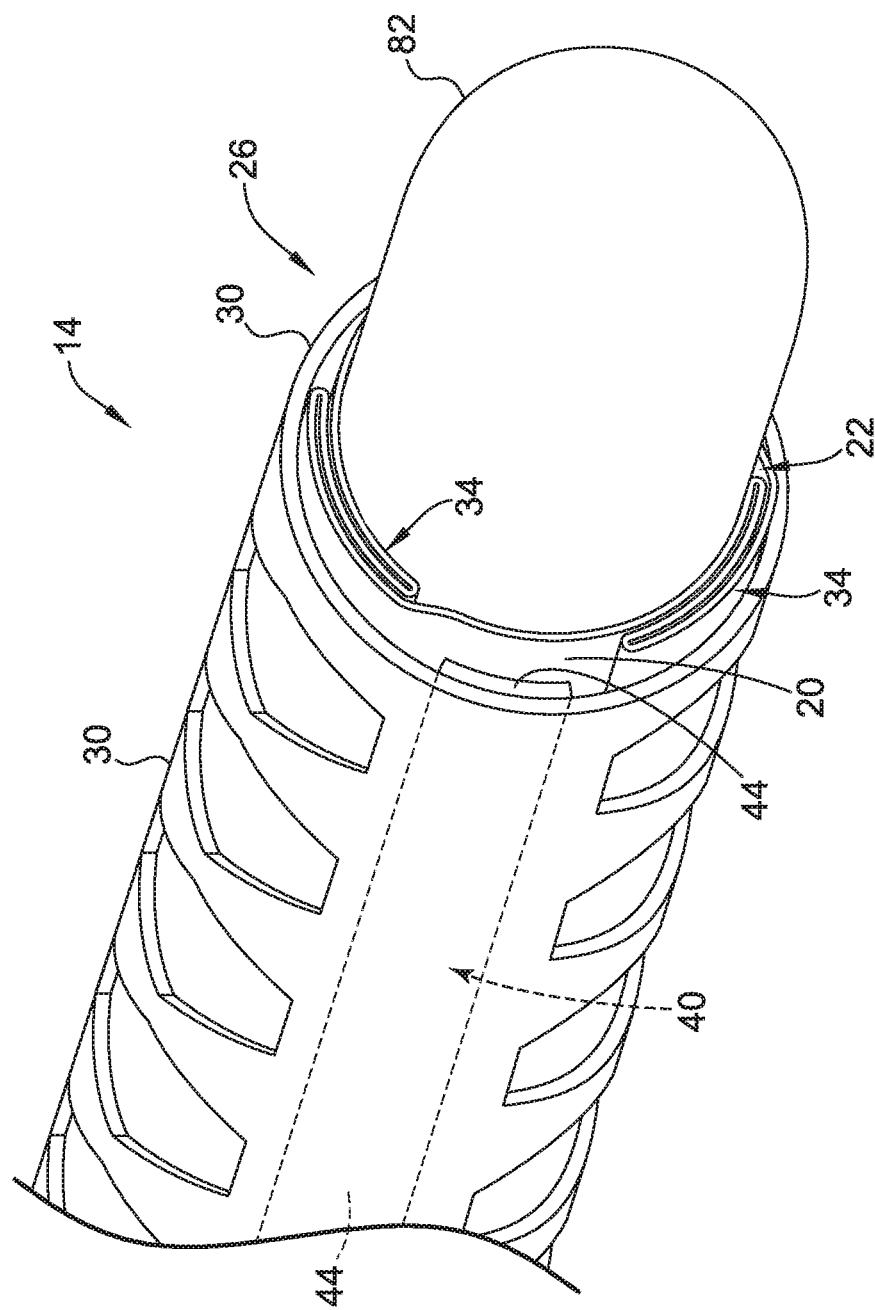

Next, the method of manufacturing the introducer 10 may include disposing the outer sheath 30 and the reinforcing member 40 (e.g., as a joined and/or fixedly attached assembly) over at least a portion of the inner liner 20 on the second mandrel 82, as shown in FIG. 8 for example, wherein the at least one perforation 32 circumferentially overlaps and/or radially aligns with each folded portion 34 of the inner liner 20. Each folded portion 34 of the at least one folded portion 34 may be circumferentially overlapped by and/or radially aligned with one of the plurality of openings 46 disposed between adjacent longitudinal spines 44 of the reinforcing member 40.

In some embodiments, a second shrink wrap may then be applied over the second mandrel 82, the outer sheath 30 and the reinforcing member 40, and the inner liner 20. The method may include joining the outer sheath 30 and the reinforcing member 40 to the inner liner 20 to form the layered tubular member 14. In some embodiments, joining the outer sheath 30 and the reinforcing member 40 to the inner liner 20 may include heating the outer sheath 30, the reinforcing member 40, and the inner liner 20 shrink-wrapped on the second mandrel 82 to induce reflow (e.g., a second reflow operation or process) of the reinforcing member 40 and/or the outer sheath 30 around the inner liner 20, thereby forming the layered tubular member 14. In some embodiments, the outer sheath 30 and/or the reinforcing member 40 may be at least partially tacked, glued, bonded, welded, or otherwise fixedly attached to the inner liner 20 prior to shrink wrapping, heating, and/or inducing reflow (e.g., the second reflow operation or process).

Heating and/or reflowing (e.g., the second reflow operation or process) the outer sheath 30 and/or the reinforcing member 40 around the inner liner 20 may permit the outer sheath 30 and/or the reinforcing member 40 to at least partially melt around and/or bond with the inner liner 20 to form the layered tubular member 14. The outer sheath 30, the reinforcing member 40, and the inner liner 20 (e.g., the layered tubular member 14) may then be removed from the second mandrel 82 as a joined and/or fixedly attached assembly. In some embodiments, the reinforcing member 40 and/or the plurality of longitudinal spines 44 may be at least partially secured and/or attached (e.g., bonded, fused, laminated, glued, co-molded, melted, welded, fixedly attached, etc.) to the inner liner 20 and/or the outer sheath 30. In some embodiments, the outer sheath 30, the reinforcing member 40, and/or the plurality of longitudinal spines 44 may be permanently attached to the outer surface of the wall of the inner liner 20. In some embodiments, the reinforcing member 40 and/or the plurality of longitudinal spines 44 may be at least partially secured and/or attached (e.g., bonded, fused, laminated, glued, co-molded, melted, welded, fixedly attached, etc.) to the inner liner 20 prior to heating and/or reflowing (e.g., the second reflow operation or process) the outer sheath 30 and/or the reinforcing member 40 around the inner liner 20. For example, in some embodiments, the plurality of longitudinal spines 44 may be bonded directly to the outer surface of the wall of the inner liner 20 prior to heating and/or reflowing (e.g., the second reflow operation or process) the outer sheath 30 and/or the reinforcing member 40. In some embodiments, heating and/or reflowing (e.g., the second reflow operation or process) the outer sheath 30 and/or the reinforcing member 40 around the inner liner 20 may permit the outer sheath 30 to melt and/or partially fill in the at least one perforation 32. For example, in some embodiments, the outer sheath 30 may have a reduced wall thickness at and/or within the at least one perforation 32. In at least some embodiments, the at least one perforation 32 may still lack a wall thickness within at least a portion of the at least one perforation 32 after the heating and/or reflowing operation. In some embodiments, the heating and/or reflowing operation may reduce the surface area of the at least one perforation 32 along the length of the outer sheath 30.

In some embodiments, the shrink wrap may be removed before removing the outer sheath 30, the reinforcing member 40, and the inner liner 20 (e.g., the layered tubular member 14) from the second mandrel 82, and in other embodiments, the shrink wrap may be removed after removing the outer sheath 30, the reinforcing member 40, and the inner liner 20 (e.g., the layered tubular member 14) from the second mandrel 82. In yet other embodiments, the shrink wrap may be left in place on the outer sheath 30, the reinforcing member 40, and the inner liner 20 (e.g., the layered tubular member 14) during and/or after removing the outer sheath 30, the reinforcing member 40, and the inner liner 20 (e.g., the layered tubular member 14) from the second mandrel 82.

In some embodiments, the outer sheath 30, the reinforcing member, and the inner liner 20 (e.g., the layered tubular member 14) may be left on the second mandrel 82. In some embodiments, the outer sheath 30, the reinforcing member 40, and the inner liner 20 (e.g., the layered tubular member 14) may be moved and/or transferred to a third mandrel. Following removal of the shrink wrap from the outer sheath 30, the reinforcing member 40, and the inner liner 20 (e.g., the layered tubular member 14), and/or placement of the layered tubular member 14 on the third mandrel, the method of manufacturing the introducer 10 may include trimming and/or cutting the layered tubular member 14 to a desired length. In some embodiments, the inner liner 20 may extend to the distal end of the layered tubular member 14.

Figure 9:
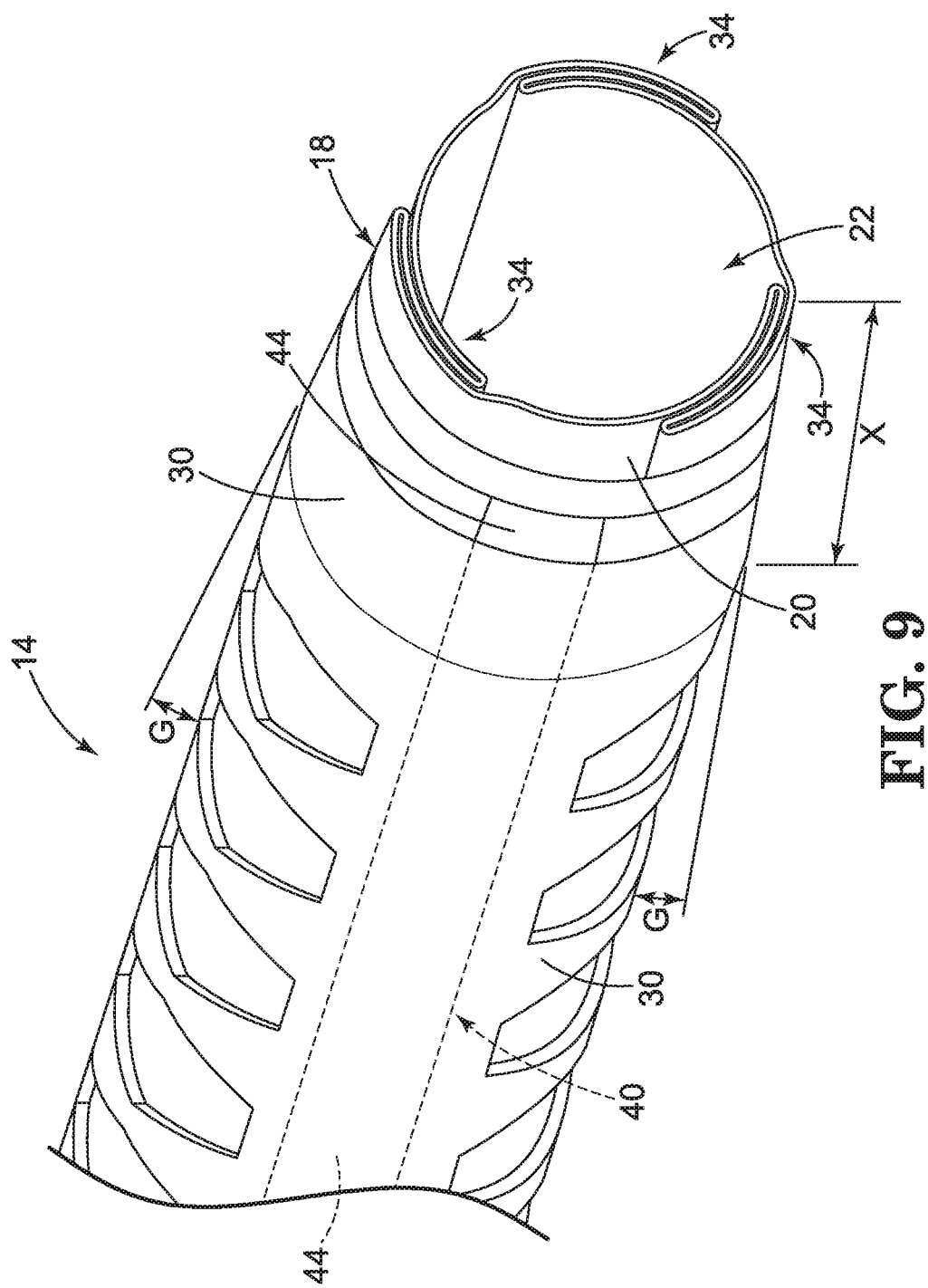

Next, the method of manufacturing the introducer 10 may further include removing material about, around, and/or from a circumference of the layered tubular member 14 of the introducer 10 adjacent the distal end of the layered tubular member 14 to form a tapered distal region 18 of the layered tubular member 14, shown in FIG. 9. The tapered distal region 18 of the layered tubular member 14 may taper in a distal direction from a first outer diameter of the layered tubular member 14 to a second outer diameter of the layered tubular member 14 less than the first outer diameter of the layered tubular member 14. In some embodiments, the first outer diameter of the layered tubular member 14 may range from about 0.039 inches (3F) to about 0.445 inches (34F), about 0.053 inches (4F) to about 0.419 inches (32F), about 0.066 inches (5F) to about 0.393 inches (30F), about 0.079 inches (6F) to about 0.367 inches (28F), about 0.092 inches (7F) to about 0.341 inches (26F), about 0.105 inches (8F) to about 0.315 inches (24F), about 0.118 inches (9F) to about 0.288 inches (22F), about 0.131 inches (10F) to about 0.263 inches (20F), about 0.144 inches (11F) to about 0.249 inches (19F), about 0.158 inches (12F) to about 0.236 inches (18F), about 0.170 inches (13F) to about 0.223 inches (17F), about 0.184 inches (14F) to about 0.210 inches (16F), and/or various subsets and/or combinations of these ranges.

In some embodiments, removing material about, around, and/or from the circumference of the layered tubular member 14 of the introducer 10 adjacent the distal end of the layered tubular member 14 may form a bevel, a taper, a chamfer, an angle, and/or a reduction in outer diameter of the layered tubular member 14 adjacent the distal end of the layered tubular member 14. For example, in some embodiments, material may be removed using grinding, turning, machining, electrodischarge machining (EDM), laser cutting, chemical dissolution, or other suitable means. The third mandrel may be configured to support the layered tubular member 14 and/or the introducer 10 during one or more of the above-referenced operations and/or processes. In some embodiments, the tapered distal region 18 may be formed at an angle G relative to the outer surface of the layered tubular member 14 and/or the introducer 10. In some embodiments, the angle G may be in a range of about 1 degree to about 75 degrees, about 1.5 degrees to about 60 degrees, about 2 degrees to about 45 degrees, about 2.5 degrees to about 30 degrees, about 3 degrees to about 15 degrees, about 3.5 degrees to about 7.5 degrees, about 4 degrees to about 6 degrees, or another suitable angle as desired, including but not limited to various subsets and/or combinations of these ranges. In some embodiments, the tapered distal region 18 may be formed and/or may extend proximally from the distal end of the layered tubular member 14 about 0.010 inches, about 0.025 inches, about 0.050 inches, about 0.075 inches, about 0.100 inches, about 0.125 inches, about 0.150 inches, about 0.175 inches, about 0.200 inches, about 0.225 inches, about 0.250 inches, about 0.300 inches, about 0.400 inches, or another suitable distance as desired. Other configurations are also contemplated.

Figure 10:
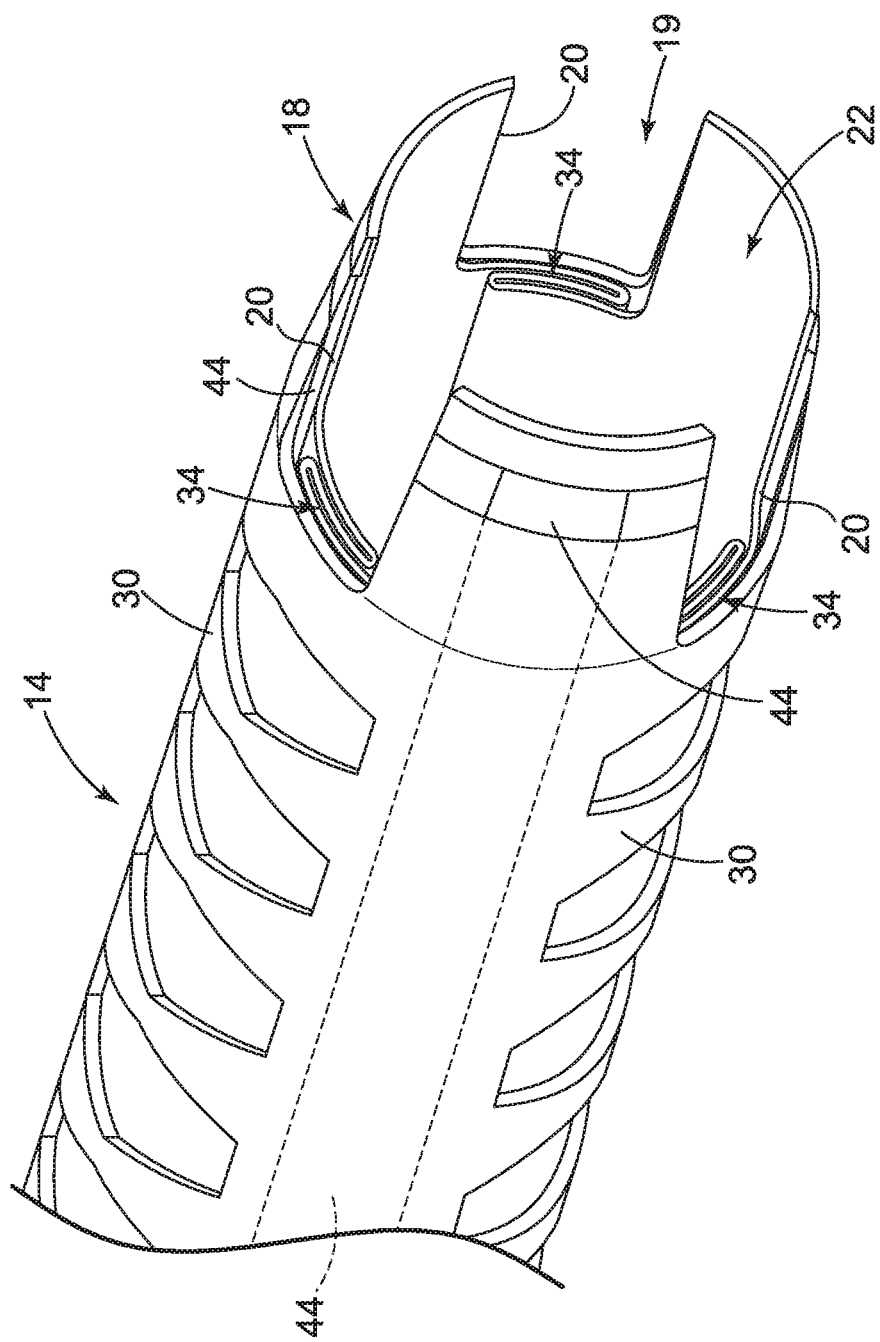

After removing material about, around, and/or from the circumference of the layered tubular member 14 of the introducer 10 to form the tapered distal region 18 of the layered tubular member 14, the method of manufacturing the introducer 10 may include modifying the tapered distal region 18 of the layered tubular member 14 by removing at least a portion of one or more of the at least one folded portion 34 from the inner liner 20 within the tapered distal region 18 of the layered tubular member 14, as seen in FIG. 10. In some embodiments, the method of manufacturing may include modifying the tapered distal region 18 of the layered tubular member 14 by removing at least a portion of each folded portion 34 from the inner liner 20 within the tapered distal region 18 of the layered tubular member 14. In some embodiments, the method may include modifying the tapered distal region 18 of the layered tubular member 14 by completely removing each folded portion 34 from the inner liner 20 within the tapered distal region 18 of the layered tubular member 14. In some embodiments, removing at least a portion of each folded portion 34 may include disposing the layered tubular member 14 of the introducer 10 on a fourth mandrel configured to support the layered tubular member 14 of the introducer 10 as the tapered distal region 18 is modified. In some embodiments, each folded portion 34 may be removed within the tapered distal region 18 by cutting, punching, machining, electrodischarge machining (EDM), chemical dissolution, laser cutting, or other suitable means. In some embodiments, removing at least a portion of each folded portion 34 from the inner liner 20 within the tapered distal region 18 may include removing portions of the outer sheath 30 that overlap each folded portion 34 within the tapered distal region 18 of the layered tubular member 14. In some embodiments, after removing at least a portion of each folded portion 34 from the inner liner 20 within the tapered distal region 18, at least a portion of each folded portion 34 terminates proximal of the distal end of the layered tubular member 14.

In some embodiments, removing at least a portion of each folded portion 34 from the inner liner 20 within the tapered distal region 18 may form at least one cut out 19 (e.g., at least one punch out, at least one notch, etc.) within the tapered distal region 18 of the layered tubular member 14, as shown in FIG. 10. In some embodiments, removing at least a portion of each folded portion 34 from the inner liner 20 within the tapered distal region 18 may include removing portions of the outer sheath 30 that overlap each folded portion 34 within the tapered distal region 18 of the layered tubular member 14 to form the at least one cut out 19 (e.g., at least one punch out, at least one notch, etc.). For example, at locations where each folded portion 34 is removed from the inner liner 20 within the tapered distal region 18 of the layered tubular member 14, the introducer 10 may be devoid of the outer sheath 30 and the reinforcing member 40, and at least a portion of each folded portion 34 may terminate proximal of the distal end of the layered tubular member 14. In some embodiments, the layered tubular member 14 may include a cut out 19 radially aligned with each folded portion 34 and extending proximally from the distal end of the layered tubular member 14 within the tapered distal region 18. In some embodiments, the at least one cut out 19 (e.g., at least one punch out, at least one notch, etc.) may have an axial or longitudinal length different from the distance the tapered distal region 18 extends proximally from the distal end of the layered tubular member 14 and/or the introducer 10. In some embodiments, the at least one cut out 19 (e.g., at least one punch out, at least one notch, etc.) may have an axial or longitudinal length substantially equal to the distance the tapered distal region 18 extends proximally from the distal end of the layered tubular member 14 and/or the introducer 10. For example, the at least one cut out 19 (e.g., at least one punch out, at least one notch, etc.) may be formed and/or may extend proximally from the distal end of the layered tubular member 14 and/or the introducer 10 about 0.010 inches, about 0.025 inches, about 0.050 inches, about 0.075 inches, about 0.100 inches, about 0.125 inches, about 0.150 inches, about 0.175 inches, about 0.200 inches, about 0.225 inches, about 0.250 inches, about 0.300 inches, about 0.400 inches, or another suitable distance as desired. In some embodiments, the at least one cut out 19 (e.g., at least one punch out, at least one notch, etc.) may be formed with a lateral and/or circumferential width of about 0.010 inches, about 0.025 inches, 0.040 inches, 0.050 inches, 0.065 inches, 0.075 inches, 0.080 inches, 0.085 inches, 0.090 inches, 0.095 inches, 0.100 inches, 0.100 inches, 0.125 inches, 0.150 inches, or another suitable distance as desired. Other configurations, shapes, arrangements, and/or dimensions are also contemplated.

In some embodiments, removing material about the circumference of the layered tubular member 14 of the introducer 10 adjacent the distal end of the layered tubular member 14 may remove a portion of the thickness of the wall of the inner liner 20 at the distal end of the layered tubular member 14. Removing each folded portion 34 of the at least one folded portion 34 from the inner liner 20 within the tapered distal region 18 also removes a portion of the reduced thickness wall of the inner liner 20, wherein any remaining portion of the wall of the inner liner 20 having a reduced thickness is supported and/or backed by the reinforcing member 40 and/or the plurality of longitudinal spines 44. The thickness of the wall of the inner liner 20 may be maintained at its full, unaltered thickness along a distal edge of the inner liner 20 disposed between adjacent longitudinal spines 44 of the reinforcing member 40, at locations where each folded portion 34 is removed from the inner liner 20 within the tapered distal region 18, and/or within the at least one cut out 19 (e.g., at least one punch out, at least one notch, etc.).

Figure 11:
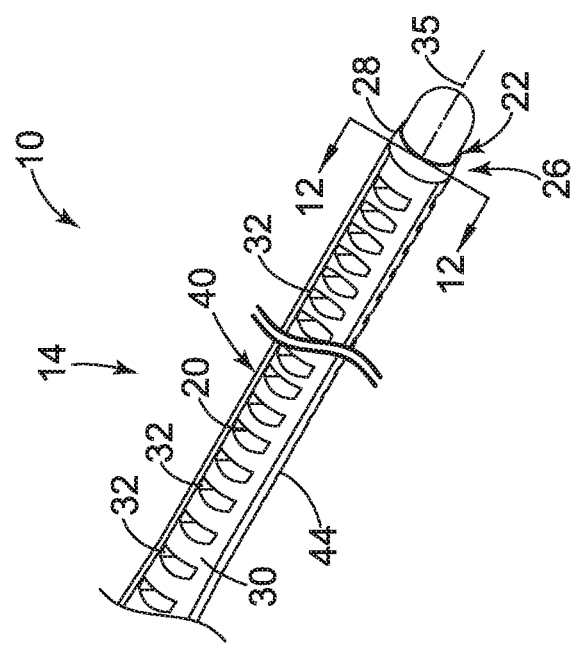

In some embodiments, after removing material from the circumference of the layered tubular member 14 of the introducer 10 to form the tapered distal region 18 of the layered tubular member 14 and removing each folded portion 34 from the inner liner 20 within the tapered distal region 18, the method of manufacturing the introducer 10 may include fixedly attaching the tip member 28 at the distal end of the introducer 10 and/or the layered tubular member 14, as seen in FIG. 11, wherein the tip member 28 is engaged with the tapered distal region 18 of the layered tubular member 14. In some embodiments, prior to fixedly attaching the tip member 28 at the distal end of the layered tubular member 14, the introducer 10 and/or the layered tubular member 14 may be disposed on a fifth mandrel, and the tip member 28 may be disposed on the fifth mandrel, as well. Heat shrink may be disposed over, on, and/or around the introducer 10 and/or the layered tubular member 14 and the tip member 28.

In some embodiments, the tip member 28 may be formed from a polymeric material having a relatively low durometer. For example, in at least some embodiments, the tip member 28 may be formed from a lower durometer material than the outer sheath 30, the reinforcing member 40, and/or the inner liner 20. In some embodiments, the tip member 28 may be formed from and/or may include a radiopaque material. For example, the lower durometer material of the tip member 28 may include and/or be doped with a radiopaque material, powder, etc. The radiopaque material may permit easy visualization of the tip member 28 by a clinician during a medical procedure. Some suitable, but non-limiting, examples of materials for the tip member 28 are discussed below.

Figure 12:
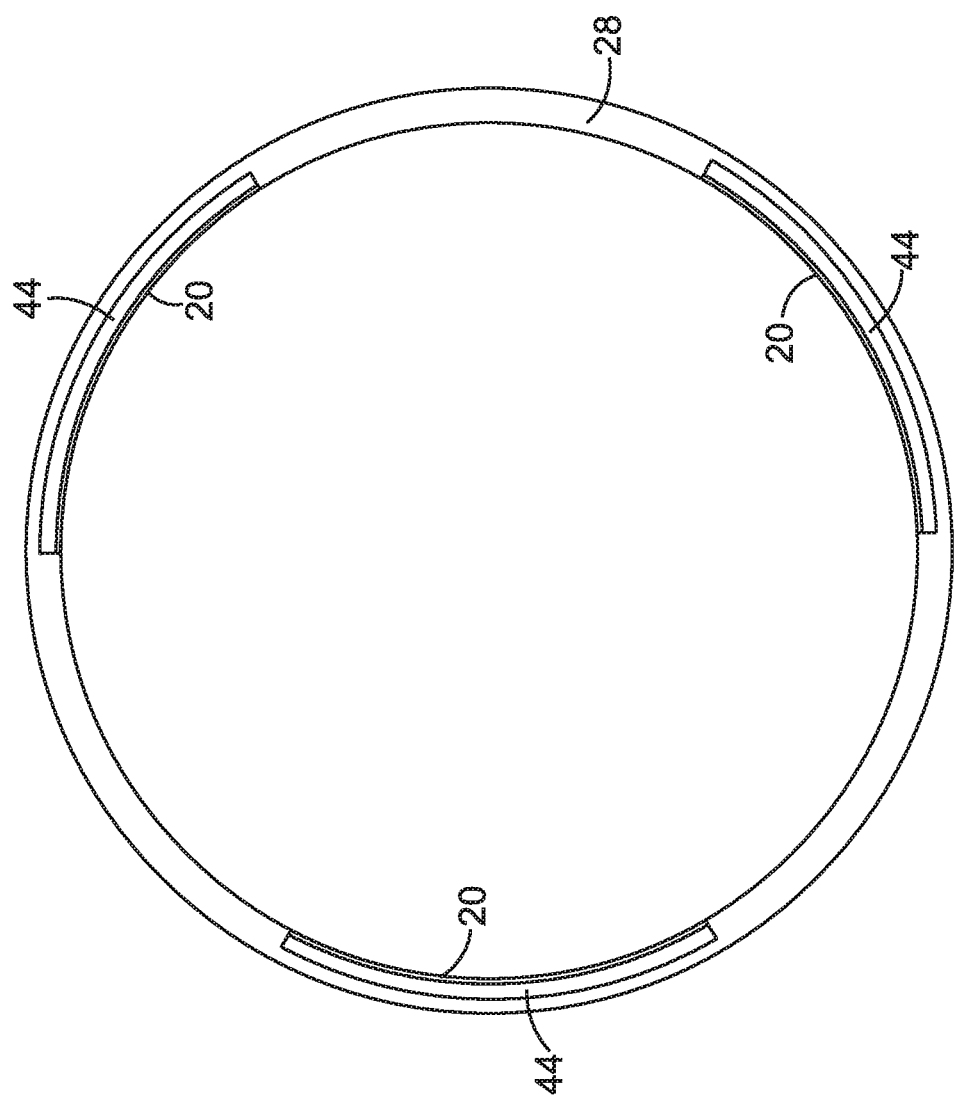
FIG. 12 is a cross-sectional view taken through the line 12-12 of FIG. 11.

In some embodiments, fixedly attaching the tip member 28 at the distal end of the layered tubular member 14 may include heating the layered tubular member 14 and the tip member 28 shrink-wrapped on the fifth mandrel to induce reflow (e.g., a third reflow operation or process) of the tip member 28 into the at least one cut out 19 (e.g., at least one punch out, at least one notch, etc.) and along the tapered distal region 18 of the layered tubular member 14, as seen in FIG. 12. After heating and/or reflowing (e.g., the third reflow operation or process) the tip member 28, an inner surface of the tip member 28 may be coincident with the inner diameter and/or the inner extent of the inner surface of the wall of the inner liner 20 in the delivery configuration and/or the folded configuration. The tip member 28 will be devoid of the at least one folded portion and/or a proximal end of the tip member 28 will abut a distal face (e.g., the wall thickness) of the at least one folded portion 34 of the inner liner 20 within the at least one cut out 19 (e.g., at least one punch out, at least one notch, etc.). In some embodiments, the tip member 28 may be at least partially tacked, glued, bonded, welded, or otherwise fixedly attached to the tapered distal region 18 prior to shrink wrapping, heating, and/or inducing reflow (e.g., the third reflow operation or process). Heating and/or reflowing (e.g., the third reflow operation or process) the layered tubular member 14 and/or the tip member 28 may permit the tip member 28 to at least partially melt around and/or bond with the tapered distal region 18 of the layered tubular member 14. The introducer 10 may then be removed from the fifth mandrel as a joined and/or fixedly attached assembly. The heat shrink may be removed from the introducer 10, after heating and/or reflowing (e.g., the third reflow operation or process) the layered tubular member 14 and/or the tip member 28, and either before or after removing the introducer 10 from the fifth mandrel. The tip member 28 may then be trimmed and/or modified to include a beveled, chamfered, and/or rounded distal edge. In some embodiments, the tip member 28 may taper in a distal direction from the first outer diameter of the layered tubular member 14 and/or the introducer 10 to a reduced outer diameter less than the first outer diameter of the layered tubular member 14 and/or the introducer 10.

In some embodiments, the tip member 28 may be configured to separate, split, perforate, and/or tear apart at locations where at least one folded portion 34 was removed from the inner liner 20 within the tapered distal region 18, and/or within the at least one cut out 19 (e.g., at least one punch out, at least one notch, etc.), when the inner liner 20 radially expands from the delivery configuration and/or the folded configuration towards the expanded configuration. In some embodiments, locations where at least one folded portion 34 was removed from the inner liner 20 within the tapered distal region 18 and/or the at least one cut out 19 (e.g., at least one punch out, at least one notch, etc.) may form a preferred and/or preferential tear line along and/or through the tip member 28 configured to split apart in response to expansion of the inner liner 20 from the delivery configuration and/or the folded configuration toward the expanded configuration.

As may be appreciated, one or more of the above described operations and/or processes (e.g., the first, second, and/or third reflow operations or processes, for example) may be combined into a single step and/or may be performed simultaneously. In some embodiments, the method of manufacturing may require more or fewer steps, mandrels, heat shrinks, heating and/or reflow operations, cutting and/or trimming operations, etc. than described herein. Other configurations and/or methods or individual steps are also contemplated.

Figure 13:
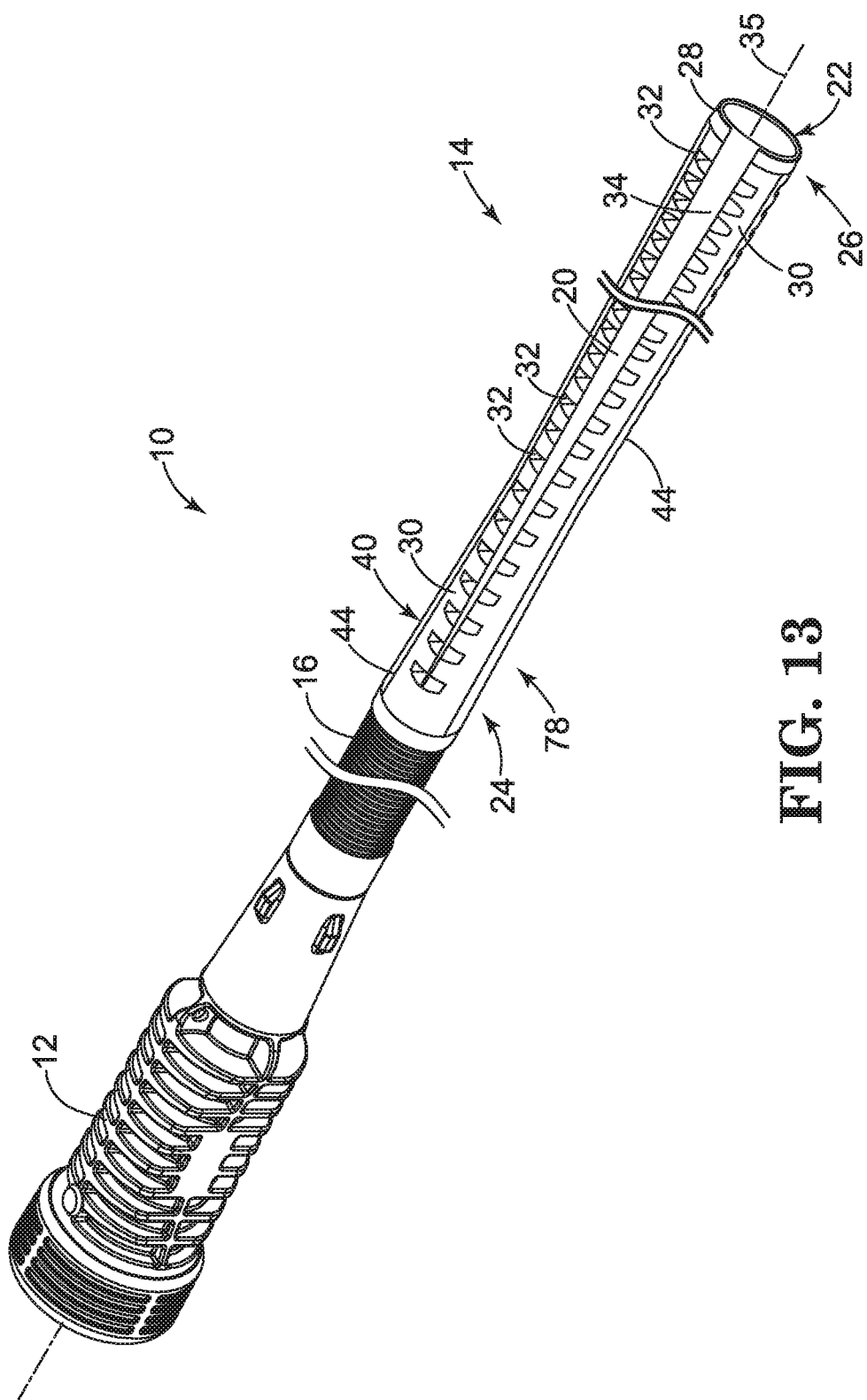
FIG. 13 illustrates aspects of the introducer of FIG. 1 during use.

When using the introducer 10, the introducer 10 may be inserted into and/or navigated within a vessel and/or body lumen to a target site or area of interest. In some embodiments, the vessel and/or body lumen may include a partial or total occlusion or obstruction formed therein. In some embodiments, the vessel and/or body lumen may be devoid of any occlusion or obstruction (partial or total). In some embodiments, the introducer 10 may be inserted into and/or navigated within the vessel and/or body lumen with a dilator disposed within the lumen 22 of the inner liner 20 and/or extending through the introducer 10. The dilator may then be removed and a medical device inserted into the lumen 22 of the inner liner 20. In some embodiments, the outer diameter of the medical device may be greater than the inner diameter and/or the inner extent of the lumen 22 of the inner liner 20 distal of the tapered region 78 in the delivery configuration and/or the folded configuration. Upon reaching and/or encountering the inner diameter and/or inner extent of the lumen 22 that is less than the outer diameter of the medical device, the medical device may begin to exert a radially outward force against the inner surface of the wall of the inner liner 20. The radially outward force may cause the inner liner 20 to radially expand towards the expanded configuration, and the outer sheath 30 may separate, split, perforate, and/or tear apart along the at least one perforation 32 and the at least one folded portion 34 may unfold thereby increasing the inner diameter and/or the inner extent of the lumen 22 of the inner liner 20. The tip member 28 may also separate, split, perforate, and/or tear apart at locations where at least one folded portion 34 was removed from the inner liner 20 within the tapered distal region 18, and/or within the at least one cut out 19 (e.g., at least one punch out, at least one notch, etc.), as the inner liner 20 radially expands from the delivery configuration and/or the folded configuration towards the expanded configuration, as shown in FIG. 13 for example.

In some embodiments, after the introducer 10 has been inserted into and/or navigated within the vessel and/or body lumen, the dilator may be inserted into the lumen 22 of the inner liner 20. In some embodiments, the outer diameter of the dilator may be greater than the inner diameter and/or the inner extent of the lumen 22 of the inner liner 20 distal of the tapered region 78 in the delivery configuration and/or the folded configuration. Upon reaching and/or encountering the inner diameter and/or inner extent of the lumen 22 that is less than the outer diameter of the dilator, the dilator may begin to exert a radially outward force against the inner surface of the wall of the inner liner 20. The radially outward force may cause the inner liner 20 to radially expand towards the expanded configuration, and the outer sheath 30 may separate, split, perforate, and/or tear apart along the at least one perforation 32 and the at least one folded portion 34 may unfold thereby increasing the inner diameter and/or the inner extent of the lumen 22 of the inner liner 20. The tip member 28 may also separate, split, perforate, and/or tear apart at locations where at least one folded portion 34 was removed from the inner liner 20 within the tapered distal region 18, and/or within the at least one cut out 19 (e.g., at least one punch out, at least one notch, etc.), as the inner liner 20 radially expands from the delivery configuration and/or the folded configuration towards the expanded configuration. The dilator may be removed from the introducer 10 and a medical device then inserted into the lumen 22 of the inner liner 20 of the introducer 10.

The materials that can be used for the various components of the introducer 10, the proximal hub 12, the layered tubular member 14, the spring member 16, the inner liner 20, the tip member 28, the outer sheath 30, the reinforcing member 40/140, etc. (and/or other systems or components disclosed herein) and the various elements thereof disclosed herein may include those commonly associated with medical devices. For simplicity purposes, the following discussion makes reference to the introducer 10, the proximal hub 12, the layered tubular member 14, the spring member 16, the inner liner 20, the tip member 28, the outer sheath 30, the reinforcing member 40/140, etc. However, this is not intended to limit the devices and methods described herein, as the discussion may be applied to other elements, members, components, or devices disclosed herein, such as, but not limited to, the plurality of longitudinal spines 44/144, etc. and/or elements or components thereof.

In some embodiments, the introducer 10, the proximal hub 12, the layered tubular member 14, the spring member 16, the inner liner 20, the tip member 28, the outer sheath 30, the reinforcing member 40/140, etc., and/or components thereof may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the introducer 10, the proximal hub 12, the layered tubular member 14, the spring member 16, the inner liner 20, the tip member 28, the outer sheath 30, the reinforcing member 40/140, etc., and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the introducer 10, the proximal hub 12, the layered tubular member 14, the spring member 16, the inner liner 20, the tip member 28, the outer sheath 30, the reinforcing member 40/140, etc. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the introducer 10, the proximal hub 12, the layered tubular member 14, the spring member 16, the inner liner 20, the tip member 28, the outer sheath 30, the reinforcing member 40/140, etc. to achieve the same result.

In some embodiments, a degree of Magnetic Resonance Imaging (Mill) compatibility is imparted into the introducer 10, the proximal hub 12, the layered tubular member 14, the spring member 16, the inner liner 20, the tip member 28, the outer sheath 30, the reinforcing member 40/140, etc. For example, the introducer 10, the proximal hub 12, the layered tubular member 14, the spring member 16, the inner liner 20, the tip member 28, the outer sheath 30, the reinforcing member 40/140, etc., and/or components or portions thereof, may be made of a material that does not substantially distort the image and create substantial artifacts (e.g., gaps in the image). Certain ferromagnetic materials, for example, may not be suitable because they may create artifacts in an MRI image. The introducer 10, the proximal hub 12, the layered tubular member 14, the spring member 16, the inner liner 20, the tip member 28, the outer sheath 30, the reinforcing member 40/140, etc., or portions thereof, may also be made from a material that the MM machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the introducer 10, the proximal hub 12, the layered tubular member 14, the spring member 16, the inner liner 20, the tip member 28, the outer sheath 30, the reinforcing member 40/140, etc., and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments, the sheath can be blended with a liquid crystal polymer (LCP). For example, the mixture can contain up to about 6 percent LCP.

In some embodiments, the introducer 10, the layered tubular member 14, the inner liner 20, the outer sheath 30, the reinforcing member 40/140, etc. disclosed herein may include a fabric material disposed over or within at least a portion of the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

In some embodiments, the introducer 10, the layered tubular member 14, the inner liner 20, the outer sheath 30, the reinforcing member 40/140, etc. may include a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyl s, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the introducer 10, the proximal hub 12, the layered tubular member 14, the spring member 16, the inner liner 20, the tip member 28, the outer sheath 30, the reinforcing member 40/140, etc. may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, antithrombin compounds, platelet receptor antagonists, antithrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:
1. An introducer, comprising:
a layered tubular member, comprising:
an inner liner including a lumen, a distal region, and at least one folded portion extending along the distal region of the inner liner in a delivery configuration;
a reinforcing member disposed over at least a portion of the inner liner, the reinforcing member having a length and including a plurality of longitudinal spines defining a plurality of openings disposed between adjacent longitudinal spines, wherein each folded portion is circumferentially overlapped by one of the plurality of openings; and
an outer sheath disposed over the reinforcing member, wherein the outer sheath includes at least one perforation circumferentially overlapping each folded portion; and
a tip member fixedly attached to a tapered distal region of the layered tubular member;
wherein the inner liner extends to a distal end of the layered tubular member;
wherein at least a portion of each folded portion terminates proximal of the distal end of the layered tubular member;
wherein the tapered distal region is devoid of each folded portion.
2. The introducer of claim 1, wherein the inner liner is configured to radially expand from the delivery configuration to an expanded configuration.
3. The introducer of claim 2, wherein the lumen has a first diameter in the delivery configuration and a second diameter in the expanded configuration, the second diameter being greater than the first diameter.
4. The introducer of claim 2, wherein at least one of the folded portions at least partially unfolds when the inner liner radially expands from the delivery configuration to the expanded configuration.
5. The introducer of claim 1, wherein the layered tubular member includes a cut out radially aligned with each folded portion and extending proximally from the distal end of the layered tubular member within the tapered distal region.
6. The introducer of claim 1, wherein the tapered distal region of the layered tubular member tapers in a distal direction from a first outer diameter to a second outer diameter less than the first outer diameter.
7. The introducer of claim 1, wherein the inner liner is formed from an inelastic material.
8. The introducer of claim 1, wherein one or more of the plurality of longitudinal spines have a substantially constant width along the length of the reinforcing member.
9. The introducer of claim 1, wherein one or more of the plurality of longitudinal spines have a distally-reducing width along at least a portion of the length of the reinforcing member.

10. An introducer, comprising:
a layered tubular member, comprising:
- an inner liner including a lumen, a distal region, and at least one folded portion extending along the distal region of the inner liner in a delivery configuration;
- a reinforcing member disposed over at least a portion of the inner liner, the reinforcing member having a length and including a plurality of longitudinal spines defining a plurality of openings disposed between adjacent longitudinal spines, wherein each folded portion is circumferentially overlapped by one of the plurality of openings; and
- an outer sheath disposed over the reinforcing member, wherein the outer sheath has a length and includes a plurality of windows radially aligned with each folded portion; and a tip member fixedly attached to a tapered distal region of the layered tubular member;

wherein the inner liner extends to a distal end of the layered tubular member;

wherein the tapered distal region is devoid of each folded portion.

11. The introducer of claim 10, wherein the tip member is configured to split apart where the tapered distal region is devoid of each folded portion when the inner liner radially expands from the delivery configuration towards an expanded configuration.

12. The introducer of claim 10, wherein the plurality of windows decreases in size from a distal end of the layered tubular member toward a proximal end of the layered tubular member.

13. The introducer of claim 10, wherein each of the plurality of windows are longitudinally separated by a distance, and wherein the distance varies along the length of the outer sheath.

14. The introducer of claim 10, wherein the inner liner has a thickness, and wherein the thickness of the inner liner is maintained along a distal edge of the inner liner between adjacent longitudinal spines.

* * * * *